(12) United States Patent
Suntych

(10) Patent No.: US 9,526,215 B2
(45) Date of Patent: Dec. 27, 2016

(54) PHOTON MODULATION MANAGEMENT SYSTEM

(71) Applicant: Xiant Technologies, Inc., Greeley, CO (US)

(72) Inventor: Jon Daren Suntych, Greeley, CO (US)

(73) Assignee: Xiant Technologies, Inc., Greeley, CO (US)

( * ) Notice: Subject to any disclaimer, the term of this patent is extended or adjusted under 35 U.S.C. 154(b) by 157 days.

(21) Appl. No.: 14/197,949

(22) Filed: Mar. 5, 2014

(65) Prior Publication Data
US 2014/0250778 A1    Sep. 11, 2014

Related U.S. Application Data

(60) Provisional application No. 61/772,856, filed on Mar. 5, 2013, provisional application No. 61/929,872, filed on Jan. 21, 2014.

(51) Int. Cl.
*A01G 7/04* (2006.01)
*A01G 33/00* (2006.01)
(Continued)

(52) U.S. Cl.
CPC ............... *A01G 7/045* (2013.01); *A01G 9/20* (2013.01); *A01G 33/00* (2013.01); *A01H 3/02* (2013.01); *C12N 13/00* (2013.01)

(58) Field of Classification Search
CPC .......... A01G 7/045; A01G 7/04; A01G 1/042; A01G 1/04; A01G 1/046; A01G 1/048; A01G 9/20; A01G 9/26
(Continued)

(56) References Cited

U.S. PATENT DOCUMENTS 2,300,727 A    11/1942    Durling
2,986,842 A     6/1961    Toulmin, Jr.
(Continued)

FOREIGN PATENT DOCUMENTS

JP    4-75779 A     3/1992
JP    9-275779 A    10/1997
(Continued)

OTHER PUBLICATIONS

Hendricks, Sterling B.; How Light Interacts With Living Matter; Scientific American, Inc.; 1968; pp. 175-186.
(Continued)

*Primary Examiner* — Son T Nguyen
(74) *Attorney, Agent, or Firm* — Cochran Freund & Young LLC; James M. Weatherly

(57) ABSTRACT

Embodiments described herein provide systems for optimizing organism growth, destruction or repair, by controlling the duty cycle, wavelength band and frequency of photon bursts to an organism, through the high frequency modulation of photons in an individual color spectrum to the organism, where the photon modulation is based upon the specific needs of the organism. Devices for the optimization of organism growth, destruction or repair through the high frequency modulation of photons of individual color spectrum to the organism are also provided. Further provided are methods for the optimization of organism growth, destruction or repair through the use of high frequency modulation of photons of individual color spectrums.

50 Claims, 17 Drawing Sheets

(51) Int. Cl.
*A01G 9/20* (2006.01)
*A01H 3/02* (2006.01)
*C12N 13/00* (2006.01)

(58) Field of Classification Search
USPC .............................. 47/58.1 LS, 1.4, 58.1 R
See application file for complete search history.

(56) References Cited

U.S. PATENT DOCUMENTS

| | | | |
|---|---|---|---|
| 3,089,280 A | 5/1963 | Klaas | |
| 3,352,058 A | 11/1967 | Brant | |
| 3,703,051 A | 11/1972 | Weinberger | |
| 3,876,907 A | 4/1975 | Widmayer | |
| 3,930,335 A | 1/1976 | Widmayer | |
| 3,931,695 A | 1/1976 | Widmayer | |
| 4,396,872 A | 8/1983 | Nutter | |
| 4,749,916 A | 6/1988 | Yamazaki et al. | |
| 5,012,609 A * | 5/1991 | Ignatius | A01C 1/00 47/1.01 R |
| 5,381,075 A | 1/1995 | Jordan | |
| 5,454,187 A | 10/1995 | Wasserman | |
| 5,675,931 A | 10/1997 | Wasserman | |
| 5,818,734 A | 10/1998 | Albright | |
| 6,615,538 B2 | 9/2003 | Hittin | |
| 7,160,717 B2 | 1/2007 | Everett | |
| 7,600,343 B2 | 10/2009 | Schultheiss et al. | |
| 8,074,397 B2 | 12/2011 | Yoneda et al. | |
| 8,181,387 B2 | 5/2012 | Loebl et al. | |
| 8,302,346 B2 | 11/2012 | Hunt et al. | |
| 8,384,047 B2 | 2/2013 | Shur et al. | |
| 2003/0009933 A1 | 1/2003 | Yoneda et al. | |
| 2004/0109302 A1 | 6/2004 | Yoneda et al. | |
| 2005/0076563 A1 | 4/2005 | Faris | |
| 2007/0151149 A1 | 7/2007 | Karpinski | |
| 2009/0007486 A1 | 1/2009 | Corradi | |
| 2009/0280223 A1 | 11/2009 | Scott | |
| 2010/0115830 A1 | 5/2010 | Dube | |
| 2010/0121131 A1 | 5/2010 | Mathes | |
| 2010/0244724 A1 | 9/2010 | Jacobs et al. | |
| 2011/0115385 A1 | 5/2011 | Waumans et al. | |
| 2011/0159562 A1 | 6/2011 | Deisseroth et al. | |
| 2011/0179706 A1* | 7/2011 | Hunt | A01G 7/045 47/58.1 LS |
| 2011/0209404 A1 | 9/2011 | Scott | |
| 2012/0042419 A1 | 2/2012 | Wilson et al. | |
| 2012/0107792 A1 | 5/2012 | Babbitt et al. | |
| 2012/0107921 A1 | 5/2012 | Willson et al. | |
| 2012/0270304 A1 | 10/2012 | Johnson et al. | |
| 2012/0293472 A1 | 11/2012 | Wong et al. | |
| 2013/0008085 A1 | 1/2013 | Aikala et al. | |
| 2013/0023044 A1 | 1/2013 | Gleason | |
| 2013/0042523 A1 | 2/2013 | Lee et al. | |
| 2013/0042527 A1 | 2/2013 | Aikala et al. | |
| 2013/0044474 A1 | 2/2013 | Aikala et al. | |
| 2013/0047503 A1 | 2/2013 | Aikala et al. | |
| 2013/0076239 A1 | 3/2013 | Chung et al. | |
| 2013/0139437 A1* | 6/2013 | Maxik | H05B 37/02 47/58.1 LS |

FOREIGN PATENT DOCUMENTS

| | | |
|---|---|---|
| JP | 10-178899 A | 7/1998 |
| WO | 2009046548 A3 | 4/2009 |
| WO | 2011086358 A2 | 7/2011 |
| WO | 2013/113096 A1 | 8/2013 |

OTHER PUBLICATIONS

PCT/US2014/20809—International Search Report and Written Opinion, Jun. 20, 2014.

* cited by examiner

PHOTON MODULATION MANAGEMENT SYSTEM

CROSS REFERENCE TO RELATED APPLICATIONS

The present application claims priority to U.S. Provisional Application No. 61/772,856, as filed on Mar. 5, 2013 and priority to U.S. Provisional Application No. 61/929,872, as filed on Jan. 21, 2014, the entire contents of both applications are herein incorporated by reference for all they teach and disclose.

BACKGROUND

Artificial light is often used in buildings, such a greenhouses and tissue culture labs, to promote organism growth, such as plant growth. Growing organisms within buildings and vertical farms require the usage of powered lighting to provide essential light for growth. These lights often are electrically powered and emit photons used for biological processes such as photosynthesis. Examples of various light or photon sources include but are not limited to metal halide light, fluorescent light, high-pressure sodium light, incandescent light and LEDs (light emitting diodes).

The foregoing examples of related art and limitations related therewith are intended to be illustrative and not exclusive, and they do not imply any limitations on the inventions described herein. Other limitations of the related art will become apparent to those skilled in the art upon a reading of the specification and a study of the drawings.

SUMMARY

The following embodiments and aspects thereof are described and illustrated in conjunction with systems, tools and methods, which are meant to be exemplary and illustrative, not limiting in scope.

An embodiment of the present invention comprises a system for enhancing growth, destruction or repair in an organism comprising at least one photon emitter in communication with a photon emission modulation controller; wherein the at least one photon emitter is configured to emit at least one first photon pulse, wherein the at least one first photon pulse has a duration, intensity, wavelength band and duty cycle; wherein the at least one photon emitter is configured to emit at least one additional photon pulse, wherein the at least one additional photon pulse has a duration, intensity, wavelength band and duty cycle, wherein the duration, intensity, wavelength band and duty cycle of the at least one additional photon pulse is different from the duration, intensity, wavelength band and duty cycle of the at least one first photon pulse, wherein the photon emission modulation controller controls the emission of photons from the photon emitter; and wherein the at least one first photon pulse and the at least one additional photon pulse induce a desired response in the organism.

Another embodiment of the present invention may comprise a method for inducing a desired response in an organism wherein the method comprises: providing at least one photon emitter; providing at least one photon emission modulation controller in communication with the at least one photon emitter; communicating a command from the at least one photon emission modulation controller to the at least one photon emitter; emitting at least one first photon pulse from the at least one photon emitters toward the organism, wherein the at least one first photon pulse has a duration, intensity, wavelength band and duty cycle; and emitting at least one additional photon pulse from the at least one photon emitters toward the organism, wherein the at least one additional photon pulse has a duration, intensity, wavelength band and duty cycle; wherein the at least one additional photon pulse has a duration, intensity, wavelength band and duty cycle, wherein the duration, intensity, wavelength band and duty cycle of the at least one additional photon pulse is different from the duration, intensity, wavelength band and duty cycle of the at least one first photon pulse.

In addition to the embodiments described above, further aspects and embodiments will become apparent by reference to the drawings and by study of the following descriptions, any one or all of which are within the invention. The summary above is a list of example implementations, not a limiting statement of the scope of the invention.

BRIEF DESCRIPTION OF THE FIGURES

The accompanying drawings, which are incorporated herein and form a part of the specification, illustrate some, but not the only or exclusive, example embodiments and/or features. It is intended that the embodiments and figures disclosed herein are to be considered illustrative rather than limiting.

DETAILED DESCRIPTION

Figure 1:
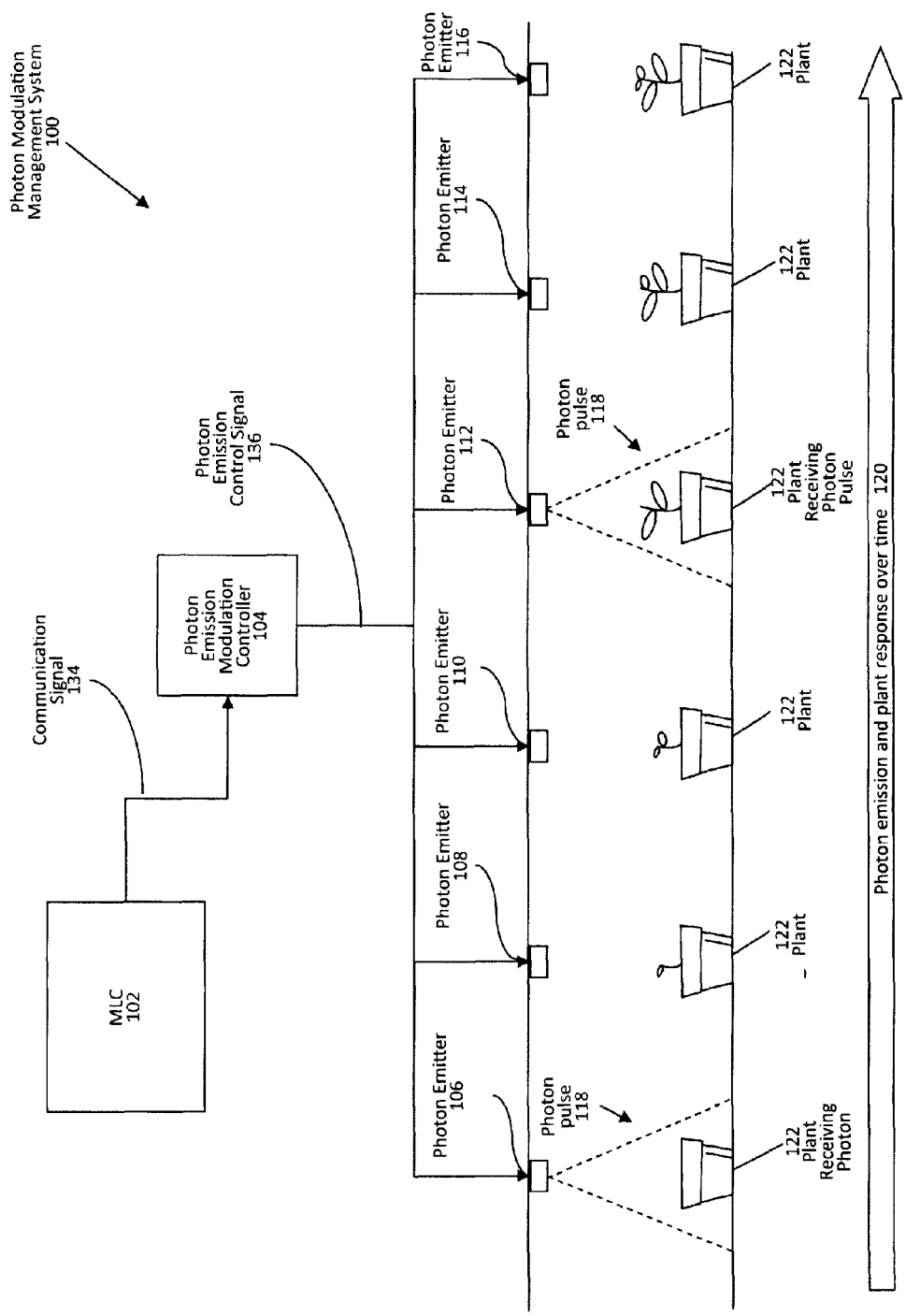
FIG. 1 is a diagram showing an example of a photon modulation growth system.

Embodiments of the present disclosure provide systems, apparatuses and methods for inducing a desired effect in an organism by creating electro-magnetic wave emission pulses (photons) of individual color spectrums in sufficient intensity to drive photochemical activation or desired response in an organism, using a characteristic frequency or pattern to minimize the required input power necessary to create organism growth, destruction and or repair, while also allowing for the monitoring of the power consumption and other variables of the system. As will be discussed in further detail, by controlling the duty cycle, wavelength band and frequency of photon bursts to an organism, the germination, growth, and reproduction rates of an organism can not only be influenced by a human, but germination, growth and reproduction rates, repair and destruction of an organism can be controlled and increased through the cycling between blue, yellow, near-red, far-red, infrared and ultra violet photon modulation.

It has long been understood that plants need 8 to 16 hours of light followed by 8 to 16 hours of dark in order to grow efficiently. The key proven concept of the present disclosure is that this basic, fundamental of plant growth is intrinsically incorrect. Plants are not capable of utilizing constant photon input during the light cycle and therefore spend an inordinate amount of energy protecting itself from the overdosing of photons.

The present disclosure, synchronizes the ability of the plant to utilize photons with the administration of photons to the plant via a timed lighting system. Specifically by combining multiple wavelengths of photons at specific combination of rates, absorption chemicals in organisms can be optimized and controlled. For example, plants spend less energy fighting excess heat and side effects such as superoxides and maximize growth by synchronizing the timing of photon pulses with the timing of chromophore absorption and transfer of photon energy to electrons through the electron transport chain. This dosage of photons to the plant is done on the order of microseconds and is followed by a dark cycle of similar magnitude. This allows the plant to devote nearly all energy to growth and basic life functions. Furthermore, specific chromophores that were thought to be slow "hormone like" control mechanisms can actually respond rapidly to further control growth.

Experimentation has proven that many of the embodiments of the present disclosure create a faster growing, sturdier, less nutrient intensive plant than that of traditional grow light systems. Each light "recipe (combination of color frequencies, modulation cycles, duty cycles, and durations)" can be optimized for each desired response to each species of organism.

The following are the major additional advantages to the methods, systems and apparatuses of the present disclosure:
a. Less Heat Creation: LED lighting intrinsically creates less heat than conventional grow lights. When LED lights are used in a dosing application, they are on less than they are off. This creates an environment with nominal heat production from the LED lights. This is not only beneficial in terms of not having to use energy to evacuate the heat from the system, but is beneficial to the plant because it does not have to use energy protecting itself from the heat and can devote that energy to growth.

b. Less Transpiration (lower water consumption)—Plant Transpiration rates go up as temperature and light intensity increase. These increased variables cause the plant cells controlling the openings (stoma) where water is released to the atmosphere to open. As plant heat and light stress is kept to a minimum with the Photon Growth Management System, stoma openings are also kept to a minimum and thus plants lose less water to transpiration.

While light is the key component of the photon modulation growth system, this system differs from other historical and even cutting edge lighting technology as it is used as the fundamental controller of plant activity rather than simply a basic element of plant growth. Likewise, while LED technology is a core component of lighting in this new system, it is a unique application of LED technology coupled with other engineering that dramatically expands the potential for reducing costs, increasing output, and enhancing control compared to existing commercial production of vegetables, ornamentals, and pharmaceutical etc. whether field or indoor, whether commercial scale or home consumer use. Via the experimentation done to date, it has been found that the same lighting system can be used to control many plant functions including germination, flowering, etc.

The systems, apparatuses and methods of the present disclosure provide energy, including individual color spectrums or ranges of color spectrums, at a frequency, intensity and duty cycle, which can be customized, monitored and optimized for the specific and optimal required growing, destruction and or repair characteristics of the target organism with the goal of maximizing growth, destruction and or repair while minimizing energy used in the system. By supplying control over the rates and efficiencies of modulated photon energy to the organism, different parts of the photochemical reaction of the organism is maximized allowing for optimal growth or the desired response (such as repairing the organism or destruction of the organism) while also allowing for control of an organisms response.

Photons are massless, elementary particles with no electric charge. Photons are emitted from a variety of sources such as molecular and nuclear processes, the quantum of light and all other forms of electromagnetic radiation. Photon energy can be absorbed by molecules called pigments, such as chromophores found in living organisms, and convert it into an electric potential.

The resulting excited pigment molecules are unstable and the energy must be dissipated in one of three possible ways. 1. as heat; 2. remitted as light; or 3. utilized through participation in a photo chemical reaction which is the focus of the present disclosure. For light to be used by plants for example, it must first be absorbed. As light is absorbed, the energy of the absorbed photon is transferred to an electron in the pigment molecule. The photon can be absorbed only if its energy content matches the energy required to raise the energy of the electron to one of the higher, allowable energy states. If matched, the electron is thus elevated from a non-excited state to one of a higher single state. In the example of a chlorophyll pigment, it has many different electrons, each of which may absorb a photon of different energy levels and consequently, different wavelengths. Moreover, each electron may exist in a variety of excitation states.

A normal excited molecule has a very short lifetime (on the order of a nanosecond) and in the absence of any chemical interaction with other molecules in its environment, it must rid itself of any excess energy and return to the ground (non-excited) state. This dissipation of excess energy is accomplished in several ways however the conversion to triplet or metastable state is the primary mechanism of the present disclosure. The excited electron is transferred to an acceptor molecule or photo-oxidation. This energy is then utilized as the primary photochemical act in photosynthesis or conformational change as in the phytochrome molecule.

Most of the photon energy absorbed by pigments never reaches a state that is utilized in a photochemical process. Because of this fact, it makes sense to synchronize the dosing of photons to the absorption capability of the plant and only give it what it can use. Pigments that absorb light for eventual use in physiological process are called photoreceptors. These molecules process the energy and informational content of photons into a form that can be used by the organism. This energy that is utilized is used to drive photosynthesis (or the reduction of carbon dioxide to carbohydrate). Different volumes and energy spectrums (or wavelengths) play a critical role in reactions.

The most common pigments utilized for plant growth are chlorophyll a, b, c, and d, phycobilins, terpenoids, carotenoids, cryptochromes, UV-B receptors (such as riboflavinoids), flavinoids, and betacyanins. These photoreceptors transfer their electrochemical energy to the electron transport chain. The photon absorbing photoreceptors such as chlorophyll, terpenoids, carotenoids etc. are actually conjugated molecules known as chromophores that allow for the conversion of photons into electrical potentials. Chromophores exist in many biological functions including melanocytosis and color sensing cells in human vision.

This phenomenon can be seen in the vision opsin chromophore in humans. The absorption of a photon of light results in the photoisomerisation of the chromophore from the 11-cis to an all-trans conformation. The photoisomerization induces a conformational change in the opsin protein, causing the activation of the phototransduction cascade. The result is the conversion of rhodopsin into prelumirhodopsin with an all-trans chromophore. The opsin remains insensitive to light in the trans form. The change is followed by several rapid shifts in the structure of the opsin and also changes in the relation of the chromophore to the opsin. It is regenerated by the replacement of the all-trans retinal by a newly synthesized 11-cis-retinal provided from the retinal epithelial cells. This reversible and rapid chemical cycle is responsible for the identification and reception to color in humans. Similar biochemical processes exist in plants. Phytochromes and pheophytins behave very similarly to opsins in that they can be rapidly regulated to switch between the Cis and Trans configurations by dosing with differing wavelengths of light.

The responses of plants to the variations in the length of day and night involve photon absorption molecular changes that closely parallel those involved in the vision cycle. Chrysanthemums and kalachoc are great examples of this. They flower in response to the increasing length of the night as fall approaches. If the night is experimentally shortened, the plants will not flower. If the plants are exposed to near red (660 nm) of light then they will not flower. If the plants are then exposed to far red (730 nm) after the exposure to near red then they will flower. It is well known that wheat, soybean, and other commercial crops are best suited or being grown in specific latitudes with different periods of light and darkness. The absorption of near red pigment (cis) converts the pigment to a far red absorption state (trans). The near red/far red chemical reversing also controls seed germination and growth cycles. These photo-absorbing chromophores in plants have been named phytochromes. It is also understood that Pheophytins (Chlorophyll a, b, and c that lack the $Mg^{2+}$ ion) also naturally exist in plants. The Pheophytins lack of double bond ring can also exhibit the cis tran configuration changes. They are control mechanisms for triggering and controlling both growth cycles and reproduction cycles. These control triggers can be altered and/or controlled by modifying the dosing of photons to cause rapid cis trans configuration changes as compared to naturally occurring or normal artificial light sources.

The photochrome molecule is made up of an open group of atoms closely related to the rings in the chlorophyll molecule. It has two side groups that can change from the cis form to the trans when they are excited by specific pulses of light, however, a shift in the position of the molecule's hydrogen atoms is more likely. The changes in the phytochrome molecule following excitation by a flash of light is similar to those in rhodopsin. These intermediate stages also involve alterations in the molecular form of the protein associated with phytochrome, just as there are alterations in the form of opsin, the protein of rhodopsin. In its final form phytochrome differs from rhodopsin in that the molecule of phytochrome remains linked to the protein rather than being dissociated from it. Far-red light will reverse the process and convert the final form of phytochrome back to its initial red-absorbing form, although a different series of intermediate molecular forms is involved. Again, these are just a few examples of how controlling the modulated pulsing of light can control/enhance growth, repair and destruction of biological organisms.

Furthermore, when organisms are subject to varying amounts of light, often in excess, the efficiency of photosynthesis is decreased and can even damage components of the electron transport chain. In the presence of excess light for example, the chlorophyll may not rapidly transfer its excitation energy to another pigment molecule and thus will react with molecular oxygen to produce a highly reactive and damaging free radical superoxide. The plant must then spend energy otherwise reserved for growth to create protecting molecules such as Carotenoids and superoxide dismutase to absorb the excess superoxides. By supplying control over the rates and efficiencies of modulated photon energy to the organism different parts of the photochemical reaction can be maximized and the amount of electric power used in the process can be reduced.

Traditional light sources, as well as sunlight, create a bottleneck insofar as energy transfer in an organism is concerned. Chromophores of chlorophyll for example absorb protons and through the electron transport chain and redox reactions to convert the energy to sugars. In each lamellae structure in chlorophyll, there is on average one sink for this energy for every 500 chlorophyll molecules. This is one example where the bottleneck in an organism is created insofar as energy transfer is concerned. Giving a plant more light does not directly mean that the plant will be able to process the extra light. In an overly simplified explanation, it is believed that phytochrome molecules are not only involved in the very slow (more hormone based) influence of germination, growth, and reproduction rates of various organisms, but also perform and regulate very fast membrane and energy sink reactions within the lamellae. Therefore, it can be assumed that controlling and altering the natural timing and synchronization of photon pulses to photochromic response will effect germination, growth, and reproduction rates of various organisms.

The present disclosure also provides methods and systems for the amount of electric power used in the process of organism growth, destruction or repair to be monitored and reduced, where the amount of energy delivered can be defined by calculating the total area under the graph of power over time. The present disclosure further provides methods and systems that allow for the monitoring, reporting and control of the amount of electric power used to grow, destroy or repair an organism, allowing an end user or energy provider to identify trends in energy use.

An embodiment of the system of the present disclosure comprises at least one photon emitter, such as a light emitting diode in communication with a photon emission modulation controller, including but not limited to a digital output signal or a solid-state relay. Photon emitters are modulated to send a pulse of photons, where each individual pulse comprises at least one color spectrum or wavelength or multiple color spectrums or a wavelength band. Each photon pulse is directed toward an organism for a duration of time, such as two milliseconds, with a duration of delay between photon pulses, such as two hundred milliseconds or up to 24 hours.

As used herein "organism" includes an assembly of molecules functioning as a more or less stable whole that exhibits the properties of life. As will be discussed further, organisms may include but are not limited to unicells and multicellular life forms, viruses, animals (including but not limited to vertebrates (birds, mammals, amphibians, reptiles, fish); mollusks (clams, oysters, octopuses, squid, snails); arthropods (millipedes, centipedes, insects, spiders, scorpions, crabs, lobsters, shrimp); annelids (earthworms, leeches); sponges; and jellyfish, microorganisms, algae, bacteria, fungi, gymnosperms, angiosperms and pteridophytes, cyanobacteria or eukaryotic green algae.

As used herein, "duty cycle" is the length of time it takes for a device to go through a complete on/off cycle. Duty cycle is the percent of time that an entity spends in an active state as a fraction of the total time under consideration. The term duty cycle is often used pertaining to electrical devices, such as switching power supplies. In an electrical device, a 60% duty cycle means the power is on 60% of the time and off 40% of the time. The duty cycle of the present disclosure may range from 0% to 93%. Far-red light will reverse the process and convert the final form of phytochrome back to its initial red-absorbing form, although a different series of intermediate molecular forms is involved. One view is that it regulates enzyme production by controlling the genetic material in cell nuclei. Another view is that the molecule's lipid solubility results in its being attached to membranes in the cell, such as the cell wall and the membrane of the nucleus. Attachment to the nucleus would then affect the permeability of the membranes and therefor the function of the cell. It is thought that in nature, the continuous exposure of an organism such as a plant to blue/near red and far-red wavelengths in the visible spectrum opposes the action of the far-red absorbing form of the phytochrome molecules. It may be that excitation by far-red light causes a continuous displacement of the far-red absorbing molecules from the cell membranes. Continuous excitation of this kind is what happens, for example during the long light periods that so markedly influence the growth of fir trees (*Abies* sp.). If fir trees are exposed to 12 hours of dark and 12 hours of light, they remain dormant. However, if the length of day increased they grow continuously. If this is intrinsically true, then the manipulation of the dosing of color spectrums to the plant can either interfere with, control, or change the natural cycles of plants that grow in natural sunlight. If for example, far-red light is dosed to the plant followed by near red dosing of the plant at shorter durations than that found in nature, the displacement of far-red absorbing molecules can be modified to accept more near red light and influence the dormancy cycles of some plants.

As used herein "frequency" is the number of occurrences of a repeating event per unit time and any frequency may be used in the system of the present disclosure. Frequency may also refer to a temporal frequency. The repeated period is the duration of one cycle in a repeating event, so the period is the reciprocal of the frequency.

FIG. 1 provides a block diagram showing an example of a photon modulation growth system 100. As shown in FIG. 1, a photon emitter 106, 108, 110, 112, 114 and 116 is shown over a period of time in communication with a photon emission modulation controller 104 for the purpose of modulating the emission of photons to an organism for a wide range of growing applications including but not limited to algal cultures, tissue cultures, germination and growth chambers, green houses, aquatic plants, supplemental lighting in such facilities and the like or tissue production. The modulated application of photons to an organism by providing photon pulses of one or more frequencies followed by pulses of one or more other frequencies for a duration along with a delay between pulses, allows for peak stimulation of an organism's biological components and responses, such as a photosynthetic organism's stoma or chlorophyll pigments and other aspects of growth regulation. Further the modulation of photons allow for the optimization of photon absorption during photosynthesis without oversaturation of the stoma or pigments. As described below, the modulation of the photon pulses increase energy and heat efficiency of current growth systems by reducing the overall power draw by the system of the present disclosure as much as 99% or more of the photon source when compared to conventional growing systems, such as a 60 watt grow light, thereby reducing the amount of power and cost used to grow an organism. In an example of the energy saving potential of the system of the present disclosure, the system pulses 49.2 watts of photons for two microseconds per 200 microseconds creating an effective power consumption of 0.49 watt-hrs/hr on the power payment meter or 0.82% of the power in a 60 watt standard incandescent bulb. In addition, because the photon emitter is not continuously emitting photons, the amount of heat produced from the photon emitter will be significantly reduced, thereby significantly reducing the cost of cooling a facility to compensate for the increased heat from lighting. The system of the present disclosure may be customized based upon organism-specific requirements for photon intensity, pulse ON duration, pulse OFF (or duty cycle), the light spectrum of the pulse including but not limited to white, near-red, yellow and blue, orange, far-red, infrared, and ultra-violet to encourage optimal growth or destruction for selected organism such as a specific plant species.

As shown in FIG. 1, a master logic controller (MLC) 102, such as solid-state circuit with digital output control or a central processing unit (CPU) is in communication with a photon emission modulation controller 104 by means of a communication signal 134. The MLC 102 provides the system of the present disclosure with input/output of the parameters and the appropriate instructions or the specialized functions for the modulation of photons from a photon emitter 106, 108, 110, 112, 114 and 116.

In a further embodiment, the MLC 102 may be hard wired or wireless to an external source such as a host, allowing external access to the MLC 102 by a host. This allows remote access by a user to monitor the input and output of the MLC 102, provide instructions or control to the systems while also allowing for remote programming and monitoring of the MLC 102.

In a further embodiment, a power measurement or power consumption sensor may be integrated or embedded into the MLC 102 in the form of an integrated circuit allowing for the measurement and reporting of the power consumption of the system based on the voltage and the current draw of the system of the present disclosure. The power consumption of the system can then be communicated either wirelessly or by hardwire from the MLC to a host. Data, including power consumption may also be sent to an outside receiver such as a database that is not connected to the system.

The photon emission modulation controller 104 receives commands and instructions from the MLC 102 including but not limited to the intensity, duty cycle, wavelength band and frequency of a photon pulse 118 from a photon emitter 106, 108, 110, 112, 114 and 116. The photon emission modulation controller 104 may be any device that modulates the quanta and provides the control and command for the intensity, duty cycle, wavelength band and frequency of a photon pulse from a photon emitter 106, 108, 110, 112, 114 and 116. A variety of devices may be used as the photon emission modulation controller 104, including but not limited to a solid-state relay (SSR), such as the Magnacraft 70S2 3V solid-state relay from Magnacraft Inc., a incandescent (Tungsten-halogen and Xenon), Fluorescent (CFL's), high intensity discharge (Metal Halide, High-Pressure Sodium, Low-Pressure Sodium, Mercury Vapor), sunlight, light emitting diodeoptical chopper and a device that induces modulation of a photon pulse. It should be understood that this description is applicable to any such system with other types of photon emission modulation controllers, including other methods to cycle a light or photon source on and off, cycling one or more colors or spectrums of light at different times, durations and intensities, such as near red, blue and far-red, allowing multiple pulses of one spectrum before pulsing another spectrum, as will be understood by one skilled in the art, once they understand the principles of this invention.

As shown in FIG. 1, based on the instructions from the MLC 102, the photon emission modulation controller 104 sends a photon emission control signal 136 to a photon emitter 106 or 112. When the photon emission control signal 136 sent to the photon emitter 106 or 112 goes ON, the photon emitter 106 or 112 emits at least one photon pulse 118 where each photon pulse comprises one color section or multiple color spectrums of light, which is transmitted to an organism 122. Then based on the instructions from the MLC 102, when the photon emitter control signal 136 sent to the photon emitter 108, 110, 112, 114 or 116 goes OFF, the photon emitter 108, 110, 112, 114, or 116 will not emit a photon pulse, and therefore no photons are transmitted to an organism 122. As shown in FIG. 1, starting from the left side of FIG. 1, the emission of photons 118 and plant 122 growth is shown over a period of time 120. The example of FIG. 1 provides a photon pulse 118 emitted from a photon emitter 106 for two (2) milliseconds with a duration of delay of two hundred (200) milliseconds before a second photon pulse 118 is emitted from the same photon emitter 112 for two milliseconds (please note that FIG. 1 is a descriptive example of photon pulses emitted over time. FIG. 1 is not drawn to scale and the amount of growth by the organism between pulses in FIG. 1 is not necessarily accurate).

As will be understood by one skilled in art, in an additional embodiment, the system as described in FIG. 1 may be completely housed in an individual photon emitter, allowing each individual photon emitter to be self-sufficient, without the need for an external control or logic unit. An example self-sufficient photon emitter may be in the form of a unit that may be connected to a light socket, or light fixtures that may be suspended above one or more organisms and connected to a power source.

The systems as shown in FIG. 1 may also take the form of a master/slave system, as will be discussed in FIG. 4, where by example, a master photon emitter containing all logic and controls for the emission of photon from master photon emitter as well as any additional photon emitters in communication with the master photon emitter.

A variety of power supplies may be used in the present disclosure, many of which would be obvious to one skilled in the art. These sources of power may include but are not limited to battery, converters for line power, solar and/or wind power. As will be understand by one skilled in the art, the intensity of the photon pulse may be static with distinct on/off cycles or the intensity may be changes of 5% or larger of the quanta of the photon pulse. The intensity of the photon pulse from the photon emitter can be controlled through the variance of voltage and/or current from the power supplies and delivered to the light source. It will also be appreciated by one skilled in the art as to the support circuitry that will be required for the system of the present disclosure, including the photon emitter control unit and the photon emitters. Further, it will be appreciated that the configuration, installation and operation of the required components and support circuitry are well known in the art. The program code, if a program code is utilized, for performing the operations disclosed herein will be dependent upon the particular processor and programming language utilized in system of the present disclosure. Consequently, it will be appreciated that the generation of program code from the disclosure presented herein would be within the skill of an ordinary artisan.

Figure 2:
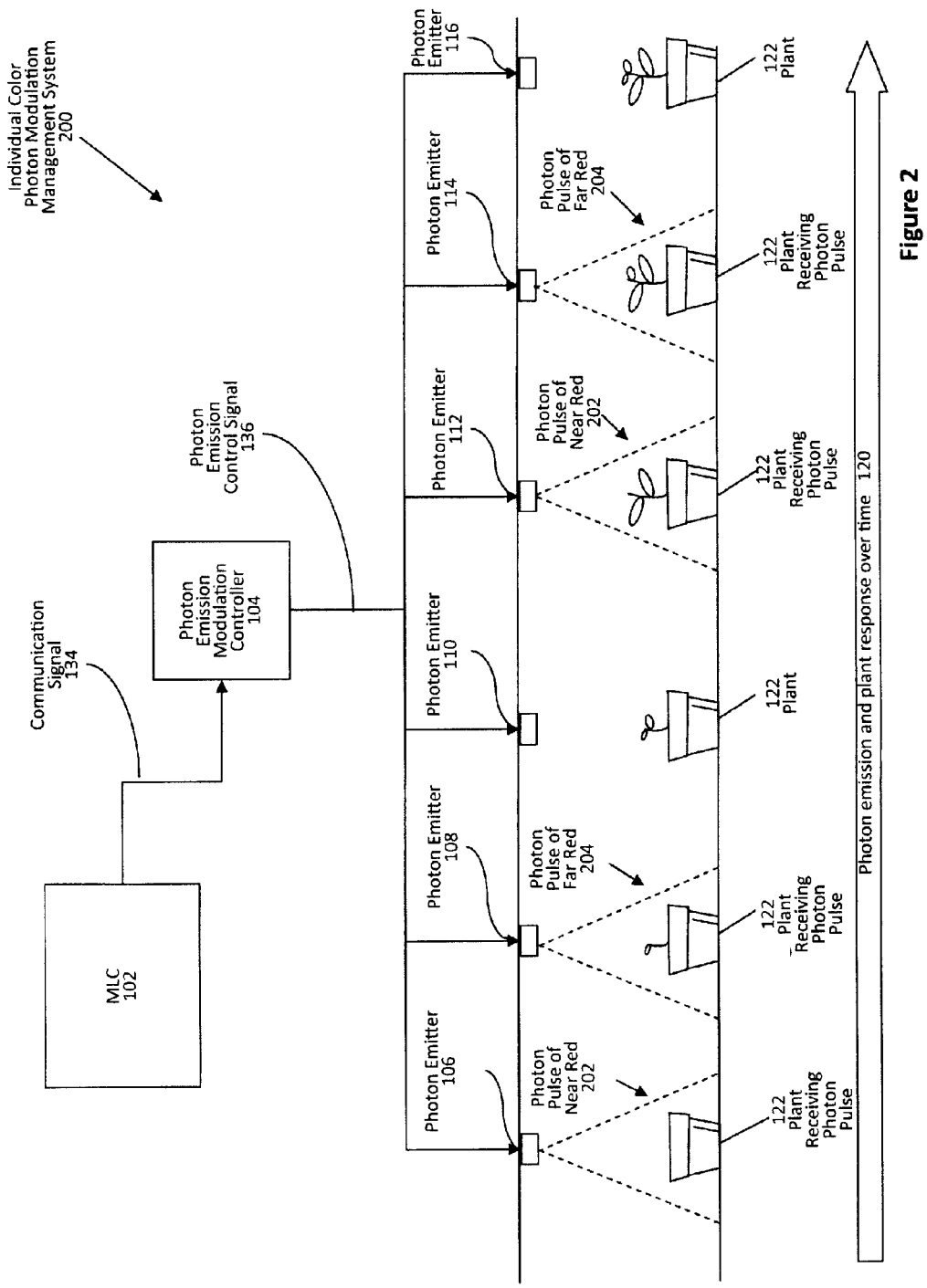
FIG. 2 is a diagram showing an example of an individual color photon modulation growth system pulsing different specific wavelength bands of light.

FIG. 2 provides a second block diagram showing an example of a photon modulation growth system 200. As shown in FIG. 2 and repeated from FIG. 1, a photon emitter 106, 108, 110, 112, 114 and 116 is shown over a period of time in communication with a photon emission modulation controller 104 for the purpose of modulating individual pulses of photons comprising individual color spectrums to an organism, including but not limited to white, near-red, blue, yellow orange, far-red, infrared, and ultra-violet color spectrums, wavelength between 0.1 nm and 1 cm. As will be understood by one skilled in the art, the present disclosure may include color spectrums of specific, individual wavelengths between 0.1 nm and 1.0 cm, or may include a range or band of wavelengths 0.1 to 200 nm in width, herein "wavelength band."

The modulation of individual color spectrums of photons to an organism by providing specific color spectrum pulses for a duration along with a delay between pulses, allows for peak stimulation of an organism's biological components and responses, such as a photosynthetic organism's stoma, chromophores, chlorophyll pigments, phototropism and other aspects of growth regulation. Examples of the ability to control specific aspects of an organism's biological components or responses through the pulsing of individual color spectrums, specific color wavelength or a range of color wavelengths may include but are not limited to:

a. the control of seed germination in some higher plants through the modulation of pulses of a specific far-red wavelengths (such as 730 nm, an example wavelength range may include 710 to 850 nm) for a period of time and then pulses of blue light (an example range may include with a range of 450 to 495 nm) in combination with near red light (such as 660 nm, an example range may include with a range of 620 to 710 nm);

b. increased growth of higher plants through the cycling of pulses of near red wavelengths with pulses of blue wavelengths and far-red wavelengths;

c. seed production in higher plants through the exposure of plants to shortened pulses of blue light after and exposure of lengthened pulses of near red light;

d. flower production where if various types of higher plants are exposed to a variation of pulses timing of far-red light (730 nm) after the exposure to pulses of near red light and blue light, the plants are induced to flower; and e. destruction of organisms such as bacteria or a virus where in an organism is exposed to a pulse of an ultra violet wavelength such as 243 nm, while the spectrum of ultra violet will be understood by one skilled in the art, an example range may include with a range between 200 and 275 nm.

The modulation of individual color spectrums, specific wavelength and a range of wavelengths of photons to an organism by providing specific color spectrum pulses for a duration along with a delay between pulses also allows for the control of non-photosynthetic growth or responses, such as phototropism in fungi or other organisms. An example may include one light or through the combination of many lights, cycling the lights on and off to control elongation and growth of an organism, such as inducing elongated growth in the stipe of a mushroom or broad cap growth in a mushroom. Another example may include using a side light source on one side of a plant more often than the other to induce a plant to grow towards that the lighted side then turn the other side on until it grows towards that light. Repeating it will cause an overall increase in growth As shown in FIG. 2 and repeated from FIG. 1, a master logic controller (MLC) 102, is in communication with a photon emission modulation controller 104 by means of a communication signal 134. The MLC 102 provides the system of the present disclosure with input/output of the parameters and the appropriate instructions or the specialized functions for the modulation of a specific individual color spectrum of photons from a photon emitter 106, 108, 110, 112, 114 and 116.

The photon emission modulation controller 104 receives commands and instructions from the MLC 102 including but not limited to the intensity, duty cycle, color spectrum and frequency of each specific color spectrum photon pulse 202 and 204 or a plurality of pulses of a specific color spectrum from a photon emitter 106, 108, 110, 112, 114 and 116. The photon emission modulation controller 104 provides the control and command for the intensity, duty cycle, color spectrum and frequency of each specific color spectrum photon pulse 202 and 204 or plurality of pulses from a photon emitter 106, 108, 110, 112, 114 and 116.

As shown in FIG. 2, based on the instructions from the MLC 102, the photon emission modulation controller 104 sends a photon emission control signal 136 to a photon emitter 106, 108, 112 or 114. When the photon emission control signal 136 sent to the photon emitter 106, 108, 112 or 114 goes ON, the photon emitter 106, 108, 112 or 114 emits one or more photon pulses of a specific color spectrum 202 or 204, which is transmitted to an organism 122. Then based on the instructions from the MLC 102, when the photon emitter control signal 136 sent to the photon emitter 110 or 116 goes OFF, the photon emitter 110 or 116 will not emit a photon pulse, and therefore no photons are transmitted to an organism 122. As shown in FIG. 2, starting from the left side of FIG. 2, the emission of photons of a specific color spectrum 202 (near red) and 204 (far-red) and plant 122 growth is shown over a period of time 120. The example of FIG. 2 provides a photon pulse or plurality of pulses of a near red color spectrum 202 emitted from a photon emitter 106 for two (2) milliseconds, followed by a photon pulse or plurality of pulses of a far-red color spectrum 204 for a duration of two (2) milliseconds with a duration of delay of two hundred (200) milliseconds of each pulse before a second photon pulse or plurality of pulses 202 is emitted from the same photon emitter 112 for two milliseconds followed by a second photon pulse or plurality of pulses of a far-red color spectrum 204 for a duration of two milliseconds from the same photon emitter 114 (please note that FIG. 2 is a descriptive example of photon pulses emitted over time. FIG. 2 is not drawn to scale and the amount of growth by the organism between pulses in FIG. 2 is not necessarily to scale).

The system of the present disclosure as described in FIGS. 1 and 2 allows for the manipulation and control of various responses by an organism through the cycling of one or more colors or spectrums of light at different times, durations and intensities, such as near red, blue and far-red, allowing single pulses or multiple pulses of one spectrum before pulsing another spectrum. The pulsing of individual color spectrums in unison or individually for a duration with a delay between pulses allows for increased efficiency and speed from seed to harvest/finish through enhanced germination and control of the progression from one plant growth stage to the next, such as control of the progression from growth, to flowering and then seed production. The system described herein provides the ability to hold a plant in a particular growth stage.

By way of example, studies have shown that using the pulse of specific color spectrums to a plant, groups of bean plants may be sown and germinated on the same date and managed identically up to the "first open flower". At this point protocols may be changed on one group to encourage and allow further development through fruit production. Protocols for the other group may be changed to "hold" at full open flower point. Within days the first group had beans ready to harvest while the other was still in open flower stage.

A variety of photon emitters may be used to provide photons, many of which are known in the art. However, an example of a photon emitter appropriate for the present discussion is a light emitting diode (LED), which may be packaged within an LED array designed to create a desired spectrum of photons. While LEDs are shown in this example, it will be understood by one skilled in the art that a variety of sources may be used for the emission of photons including but not limited to metal halide light, fluorescent light, high-pressure sodium light, incandescent light and LEDs (light emitting diode). Please note that if a metal halide light, fluorescent light, high-pressure sodium light, incandescent light is used with the methods, systems and apparatuses described herein, the proper use of these forms of photon emitters would be to modulate and then filter the light to control what wavelength for what duration is passed through.

Embodiments of the present disclosure can apply to LEDs having various durations of photon emissions, including durations of photon emissions of specific color spectrums and intensity. The pulsed photon emissions of specific color spectrums may be longer or shorter depending on the organism in question, the age of the organism and how the emission will be used in facilitating biochemical processes for organism growth.

The use of an array of LEDs may be controlled to provide the optimal photon pulse of one or more color spectrums for specific organism growth such as growing lettuce or for tomato growth. The user may simply select the photon pulse intensity, color spectrum, frequency and duty cycle for a particular type of organism to encourage efficient biological responses such as photosynthetic process in plants. LED packages can be customized to meet each organism's specific requirements. By using packaged LED arrays with the customized pulsed photon emission, as discussed above, embodiments described herein may be used to control light to alter the vitamin, salt, acid, antioxidant, flavonoid, carotenoid, water, chloroplast and accessory pigment and absorption levels within the target organism.

Figure 3:
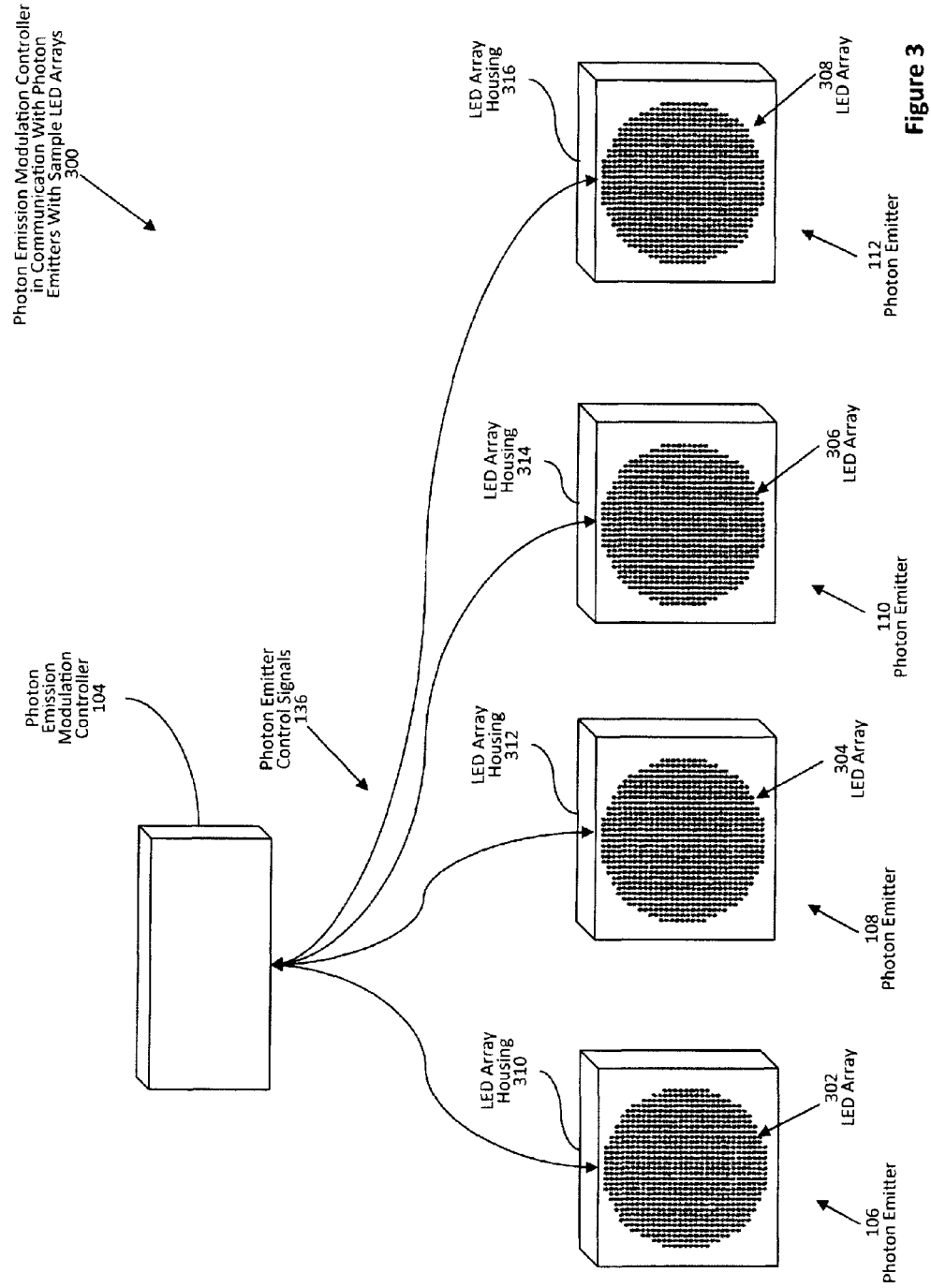
FIG. 3 is a diagram showing a photon emission modulation controller in communication with a plurality of photon emitters with sample LED arrays.

FIG. 3 is a diagram of an example of a plurality of photon emitters 106, 108, 110 and 112 with LED arrays 300. As shown in FIG. 3, a photon emission modulation controller 104 is in communication by means of a plurality of photon emitter control signals 136 with a plurality of photon emitters 106, 108, 110 and 112 (which are the same photon emitters that are shown in FIG. 1). As further shown in FIG. 3, each photon emitter 106, 108, 110 and 112 comprises an array of LEDs 302, 304, 306 and 308. Each array of LEDs 302, 304, 306 and 308 and the circuitry to allow for the array of LEDs to communicate with the photon emission modulation controller 104 are contained in an LED array housing 310, 312, 314 and 316.

As shown in FIG. 3, the shape of LED array is a circle, however as will be understood by one skilled in the art, the shape of the array may take a variety of forms based upon the needs of the organisms such as plants, the volume of organisms such as plants to receive a pulse of photons and a variety of other conditions. The shape of the array may include but is not limited to, circular, square, rectangular, triangular, octagonal, pentagonal and a variety of other shapes.

The LED array housing 310, 312, 314 and 316 for each photon emitter 106, 108, 110 and 112 may be made of a variety of suitable materials including, but are not limited to, plastic, thermoplastic, and other types of polymeric materials. Composite materials or other engineered materials may also be used. In some embodiments, the housing may be made by a plastic injection molding manufacturing process. In some embodiments, the housing may be transparent or semi-transparent and in any color.

Figure 4:
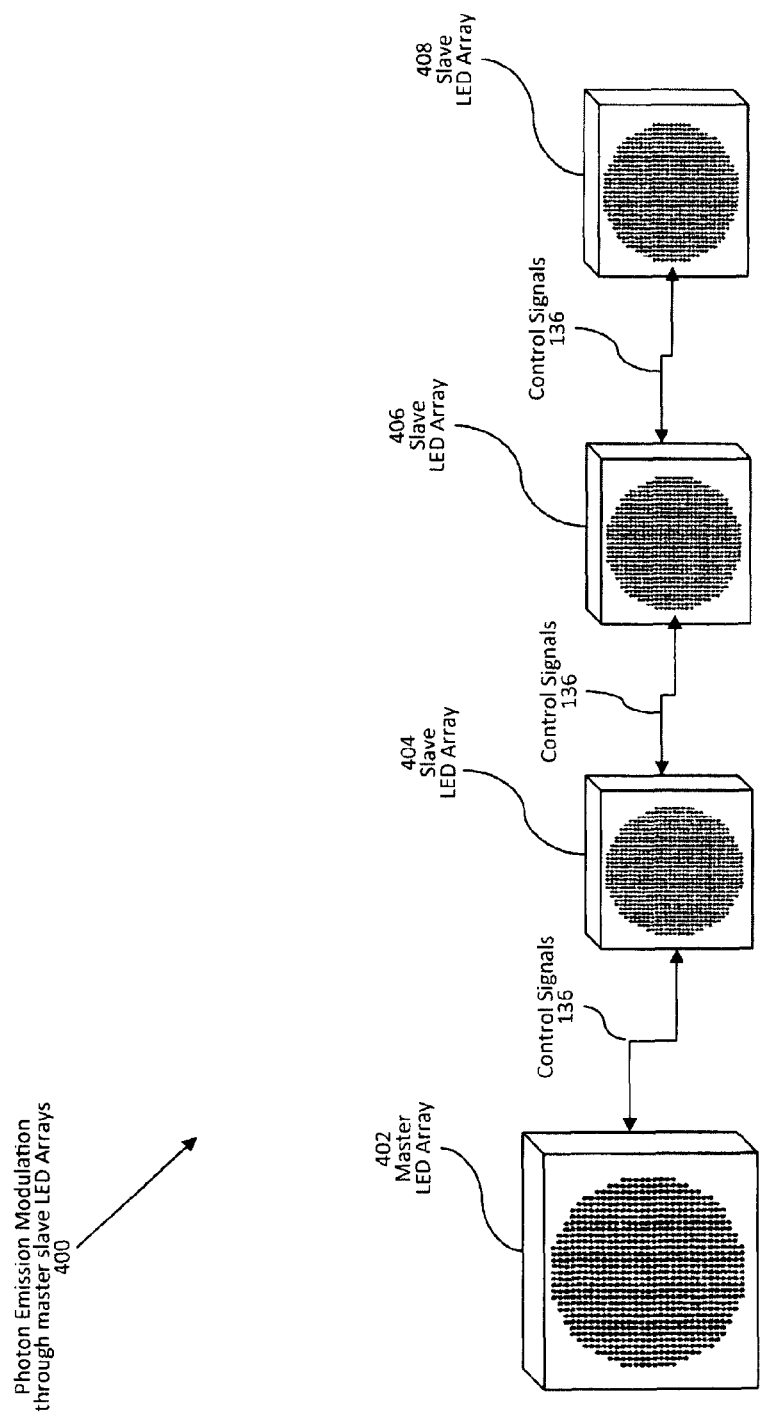
FIG. 4 is a diagram showing photon emission modulation through a master/slave LED array.

FIG. 4 is a diagram of an example of a plurality of photon emitters with a master photon emitter in communication and control of one or more slave photon emitters, 400. As shown in FIG. 4, a master photon emitter 402 is in communication by means of a photon control signal 136 with a series of slave photon emitters 404, 406, and 408. The master photon emitter 402 contains a controller, such as the MLC (102 of FIGS. 1 and 2), as well as photon emission modulation controller (shown as 104 FIGS. 1 and 2) which controls the intensity, duty cycle and frequency of each specific color spectrum photon pulse from an array of LEDs housed within the master photon emitter 402 while also allowing the master photon emitter to control the intensity, duty cycle and frequency of each specific color spectrum photon pulse from each slave photon emitters 404, 406, and 408.

Conversely, each slave photon emitter 404, 406, and 408 contains the circuitry to receive command signals 136 from the master photon emitter 402 and the circuitry necessary to emit a pulse of a specific spectrum from an array of LEDs (such as near red, far-red, blue or yellow) housed within each slave photon emitter 404, 406, and 408. For clarity, each slave photon emitter does not contain a controller such as the MLC nor does the slave photon emitter 404, 406, and 408 contain a photon emission modulation controller. All commands and controls for the slave photon emitter 404, 406, and 408 are received from the master photon emitter 402. This master/slave system allows for sharing of a single power supply and microcontroller. Master has the power supply and that power is also transferred to the slaves. Additionally, the master/slave system can be utilized to pulse photons in patterns to help stimulate the photoperiodism or phototrophic response in other organisms response in plants.

A bus system may be included in MLC of the master photon emitter 402 or in each slave photon emitter 404, 406 and 408 to allow for the specific control by the master photon emitter 402 of each individual slave photon emitter 402, 404 and 408. By way of example, the master photon emitter 402 may send a signal 136 to a specific slave photon emitter 404 commanding the slave photon emitter 404 to emit a far-red pulse for a specific duration, while the master photon emitter 402 simultaneously sends a command signal 136 to a second slave photon emitter 406 to emit a near red pulse for a specific duration. While this descriptive example shows an array, plurality or chain of three slave photon emitters 402, 404 and 406 in communication with a master photon emitter 402, it should be understood that this description is applicable to any such system with any number of slave photon emitters in communication and under the control of a master photon emitter, as will be understood by one skilled in the art, once they understand the principles of this invention.

In a further embodiment, the master photon emitter 402 may be hard wired or wireless to allow external access to the master photon emitter 402 by a host, allowing remote access to monitor the input and output of the master photon emitter 402 while also allowing for remote programming of the master photon emitter.

Figure 5:
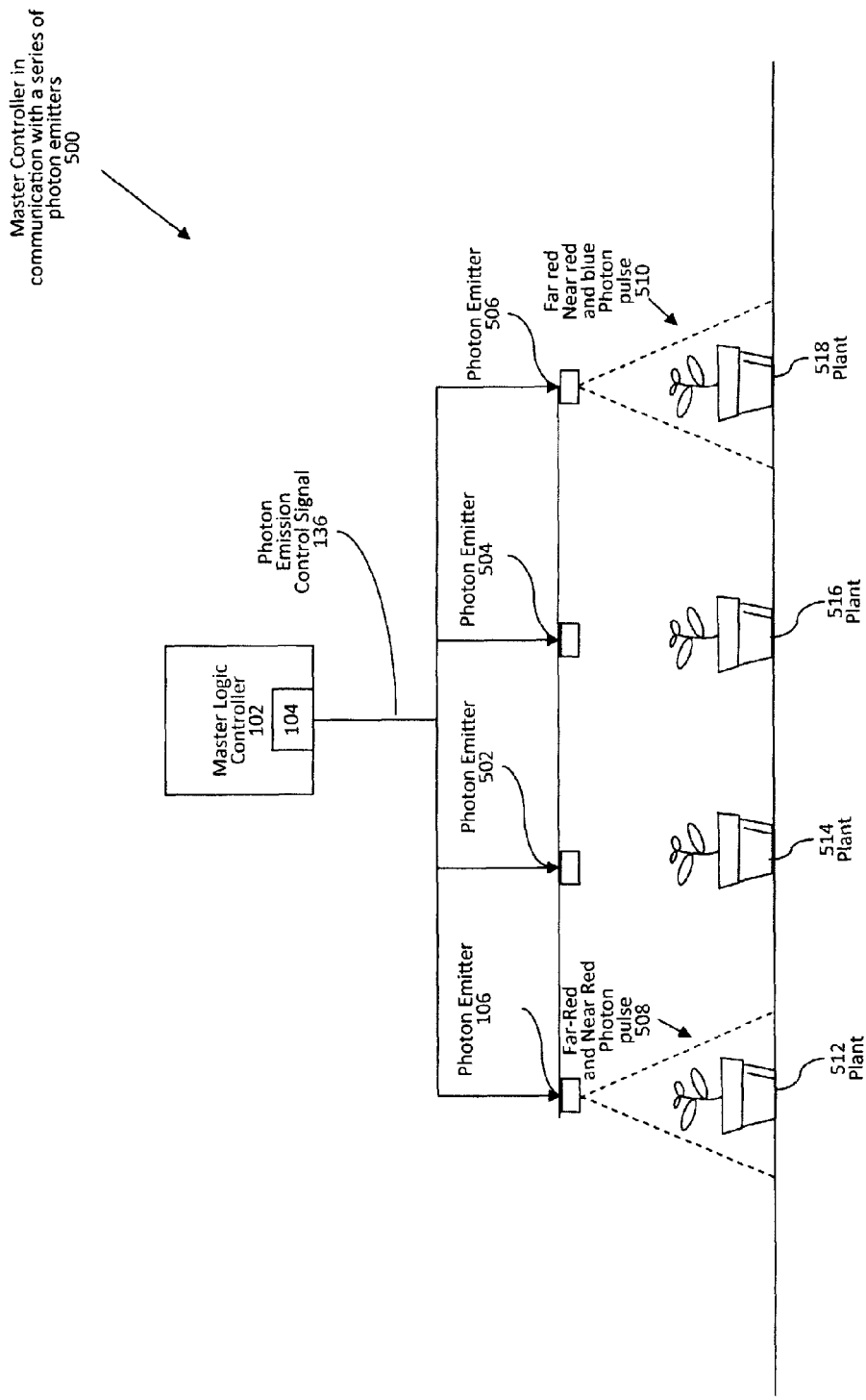
FIG. 5 is a diagram showing a photon emission in communication and control of a series of photon emitters.

FIG. 5 is a diagram of an example of a master logic controller in communication and control of one or more photon emitters, 500. As shown in FIG. 5, a master logic controller 102 is in communication by means of a photon emission control signal 136 with a series of photon emitters 106, 502, 504 and 506 located above four plants 512, 514, 516 or 518. In this example, the master logic controller or MLC 102 (as previously discussed in FIGS. 1, 2 and 3) also contains a photon emission modulation controller 104 (shown discussed in FIGS. 1, 2 and 3) which allows the MLC 102 to control the intensity, duty cycle and frequency of each specific color spectrum photon pulse from an array of LEDs housed within each photon emitter 106, 502, 504 and 506.

Through the photon emission modulation controller 104, the MLC 102 communicates commands and instructions to each photon emitter 106, 502, 504 and 506 including but not limited to the intensity, duty cycle and frequency of each specific color spectrum photon pulse 508 and 510 from each photon emitter 106, 502, 504 and 506. The MLC 102 also maintains control of the power supply to the system and control the transfer of power to each individual photon emitter 106, 502, 504 and 506.

As shown in FIG. 5, based on the instructions from the MLC 102, the photon emission modulation controller 104 sends a photon emission control signal 136 to each individual photon emitter 106, 502, 504 and 506. Based on the specific instructions sent to each photon emitter 106, 502, 504 and 506, individual photon emitters 106 or 506 may pulse one or more specific color spectrums 508 and 510 to an organism 512, 514, 516 or 518 (such as a pulse of both far-red and near red 508 at various durations or a pulse of far-red, near red and blue at various durations 510). As further shown in FIG. 5, based on the instructions from the MLC 102, other individual photon emitters 502 or 504 may not emit a photon pulse toward an organism 122 for a duration.

The ability of the MLC 102 to control the photon output or emitted from each individual photon emitter 106, 502, 504 and 506 allows the system of the present disclosure to modify the photon emission to an organism based on the specific needs or requirements for an organism. As discussed in association with FIG. 2, by way of example, the MLC may be programmed to issue a signal to a specific emitter for modulation of pulses of far-red light for a period of time followed by pulses of blue light in combination with near red light for the control of seed germination in some higher plants or the MLC may issue a command to a specific photon emitter for the cycling of pulses of near red light with pulses of blue light and far-red light to increase the growth of specific plants. In another example, the MLC may issue a signal to a specific photon emitter for the pulsing of blue light after an exposure of pulses of near red light in repetition in order to induce a plant to produce seed or the MLC may send a signal to a specific photon emitter for a pulse of far-red light after the exposure to pulses of near red light in repetition in order to induce a plant to flower.

In the example shown in FIG. 5, all commands and controls for each photon emitter 106, 502, 504 and 506 are received externally from the MLC 102. However, as will be understood by one skilled in the art, the logic and hardware associated with the MLC 102 and photon emission modulation controller 104 may also be housed within each individual photon emitter, allowing each individual photon emitter to be self-sufficient, without the need for an external control or logic unit.

In a further embodiment, the MLC 102 may be hard wired or wireless, allowing external access to the MLC 102 by a user. This allows remote access by a user to monitor the input and output of the MLC 102 while also allowing for remote programming of the MLC.

Figure 6:
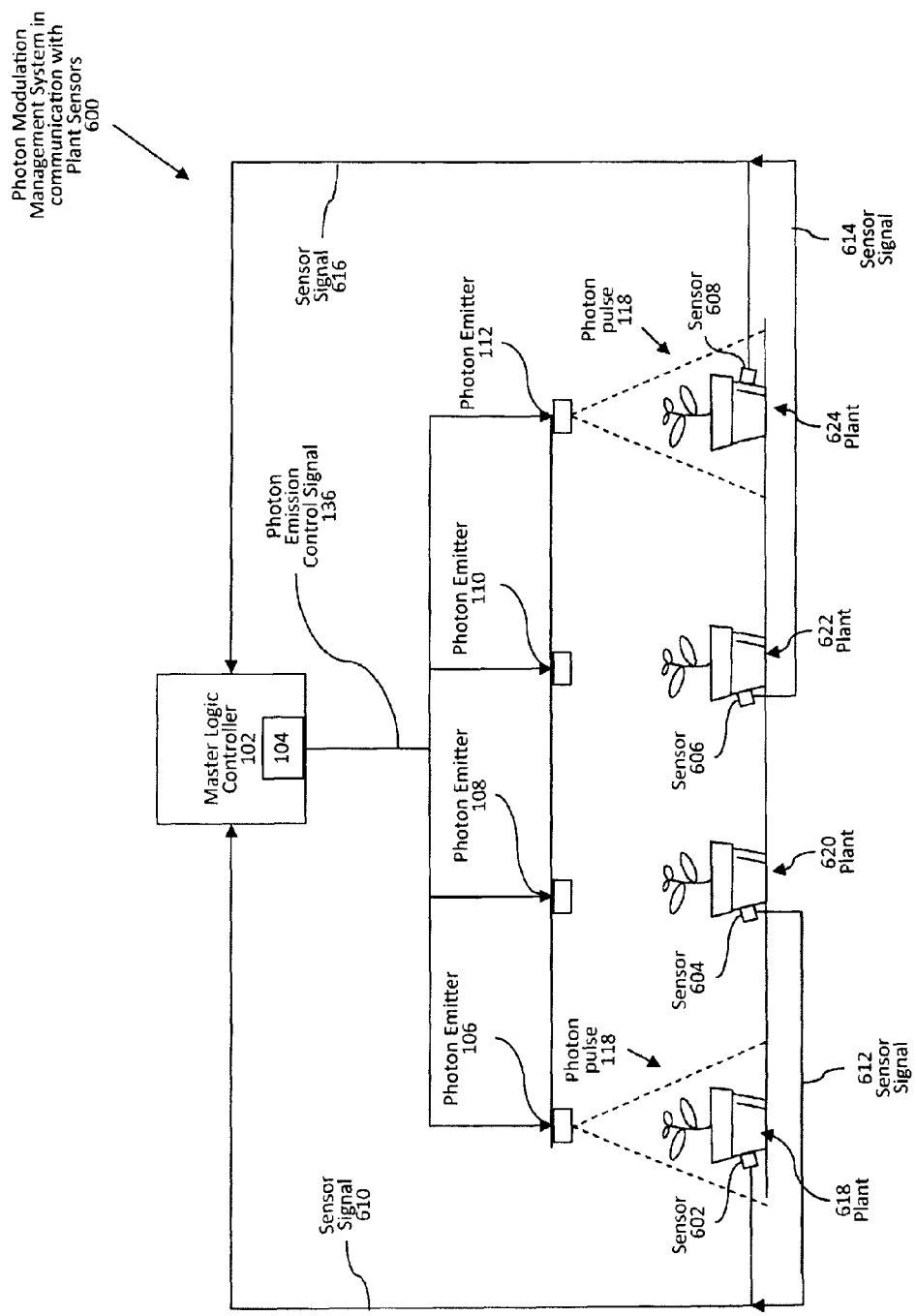
FIG. 6 is a diagram showing a photon emission growth system in communication with a series of plant sensors.

FIG. 6 provides an example of a further embodiment, showing the photon modulation system of the present disclosure where one or more sensors are used to monitor an organism's environmental conditions as well as the organism's responses 600. As shown in FIG. 6, one or more sensors 602, 604, 606 and 608 are associated with each plant 618, 620, 622, and 624 in order to monitor various conditions associated with the plant 618, 620, 622, and 624. The conditions associated with the plant or organism which may be monitored include but are not limited to, soil moisture, air temperature, leaf temperature, pH, stem or fruit diameter, gas, photorespiration, respiration of an organism or sap flow within the plant. As will be understood by one skilled in the art, the sensors may include but are not limited to: a stem diameter sensor, a fruit diameter sensor, a leaf temperature sensor, a relative-rate sap sensor, an infrared sensor, gas, photorespiration sensor, respiration sensor, camera, near-infrared sensor or pH sensor.

The sensors 602, 604, 606 and 608 monitor one or more conditions associated with the plant or organism 618, 620, 622, and 624 and then transmit the data 610, 612, 614 or 616 to the MLC 102. Transferring the data from the one or more sensors 602, 604, 606 and 608 to the MLC 102 can be accomplished in a number of ways, either wirelessly or hard wired. As will be understood by one skilled in art, a variety of communication systems may be used for the delivery of sensor-derived information from the plant 618, 620, 622, and 624 to the a MLC 102.

The data from the one or more sensors 602, 604, 606 and 608 is analyzed by the MLC 102. Based on the information from the sensors, the MLC 102, through the photon emission modulation controller 104, the MLC 102 is able to adjust the intensity, duty cycle and frequency of each specific color spectrum photon pulse 608 and 610 of each individual photon emitter 106, 602, 604 and 606, or to adjust the intensity, duty cycle and frequency of a group of photon emitters based on the needs of the individual plants 618, 620, 622, and 624 associated with a specific sensor 602, 604, 606 and 608 or the needs of the plants as a whole. An example may include adjusting a pulse to comprise both blue and near red 608 at various durations or adjusting duration of a pulse of far-red, near red and blue 610.

In additional embodiments, the system of the present disclosure may also include a watering system, fertilizing system and/or a fertigation system (not shown in FIG. 7) in communication and under the control of the MLC 102 or a separate logic controller. Based on information from the sensors 602, 604, 606 and 608 associated with each plant or organism, the MLC 102 is able to communicate with an irrigation system, nutrient system, nutrient source or fertigation system in order stop and start an irrigation, fertilizing or fertigation event to a plant or an organism, as well adjust the timing or concentration of a watering, fertilizing or fertigation event that will be sent to a plant or an organism. Data, including power can be sent to an outside receiver such as a database that is not connected to the system.

Examples of an irrigation system may include drip irrigation, overhead misting, or fog systems. Examples of nutrient systems or nutrient sources may include nutrient injection, nutrient film, nutrient drips or fertigation (a combination of fertilizer and irrigation) where the nutrient source is instructed or is able to provide a nutrient event to an organism by means of directing nutrients to the organism.

Figure 7:
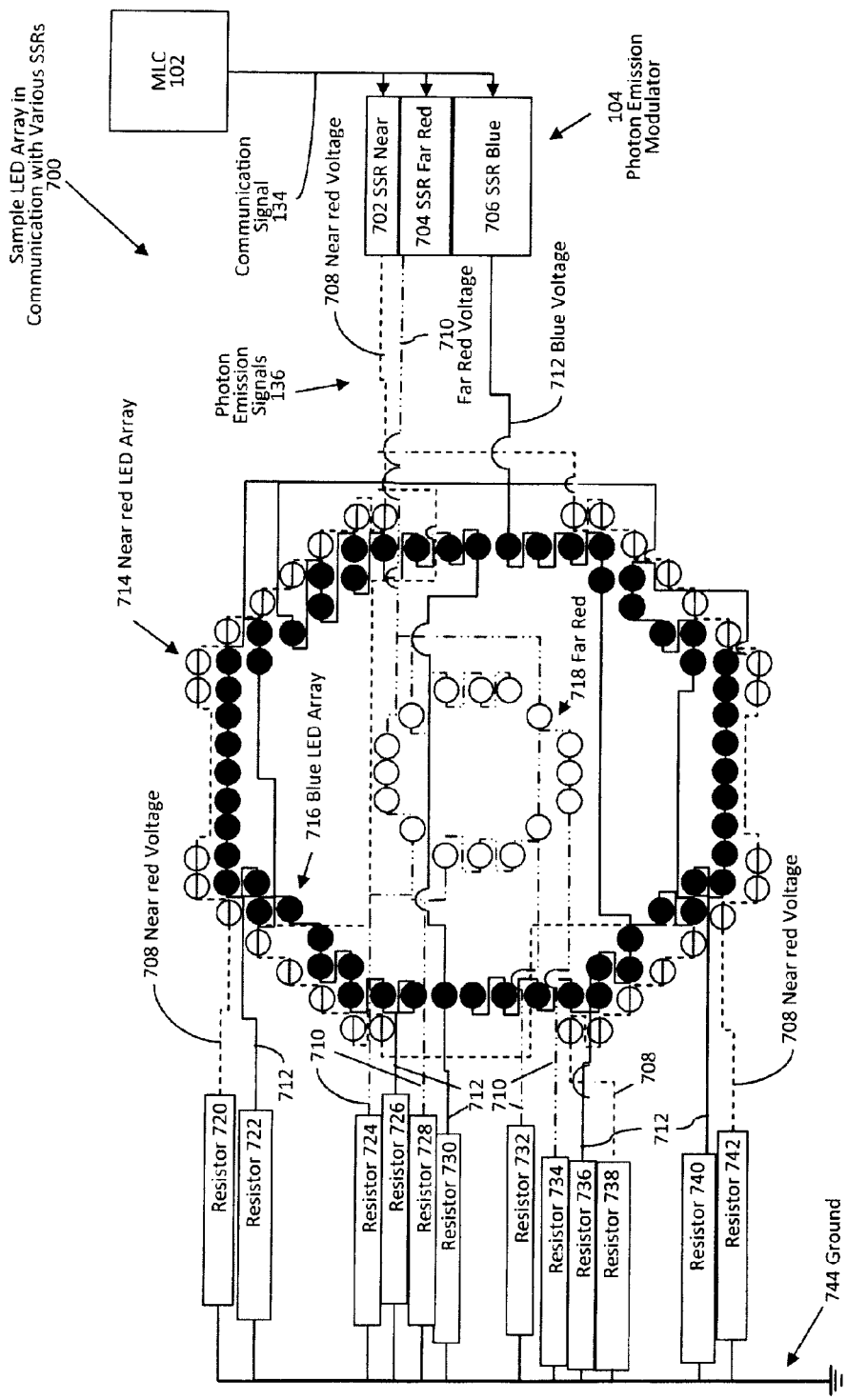
FIG. 7 is a diagram showing a sample LED array in communication with various SSRs (Solid State Relays) or FETS.

FIG. 7 is an example of one embodiment of an array of LEDs in communication with a series of solid-state relays or SSRs 700. As shown in FIG. 7 and repeated from FIG. 1, a MLC 102 is in communication by means of a communication signal 134 with a photon emission modulation controller 104. The photon emission modulation controller 104 of this example contains three solid-state relays. The MLC 102 outputs a signal to control the SSRs. The first solid-state relay controls an array of near red LEDs 702, the second solid-state relay controls an array of far-red LEDs 704 and the third solid-state relay to controls an array of blue LEDs 706. Each solid-state relay 702, 704 and 706 is in communication with an array of LEDs, 714, 716 and 718 by means of a photon emission signal 136. As shown in FIG. 7, the near red solid-state relay 702 sends a photon emission signal 136 to initiate a photon pulse of the near red LEDS 714 comprising a near red voltage 708 to an array of near red LEDs 714. The near red voltage 708 is then transmitted from the array of near red LEDs 714 to a series of resistors 720, 742, 738, such as a 68 ohm resistor, with each resistor 720, 742 and 738 connected to a ground 744.

As further shown in FIG. 7, the far-red solid-state relay 704 sends a photon emission signal 136 to initiate a photon pulse of far-red LEDs comprising a far-red voltage 710 to an array of red LEDs 718. The red voltage 710 is then transmitted from the red LED array 718 and a series of resistors 724, 728, 732 and 734, such as 390 ohm resistor with each resistor 724, 728, 732 and 734 connected to a ground 744.

Figure 8:
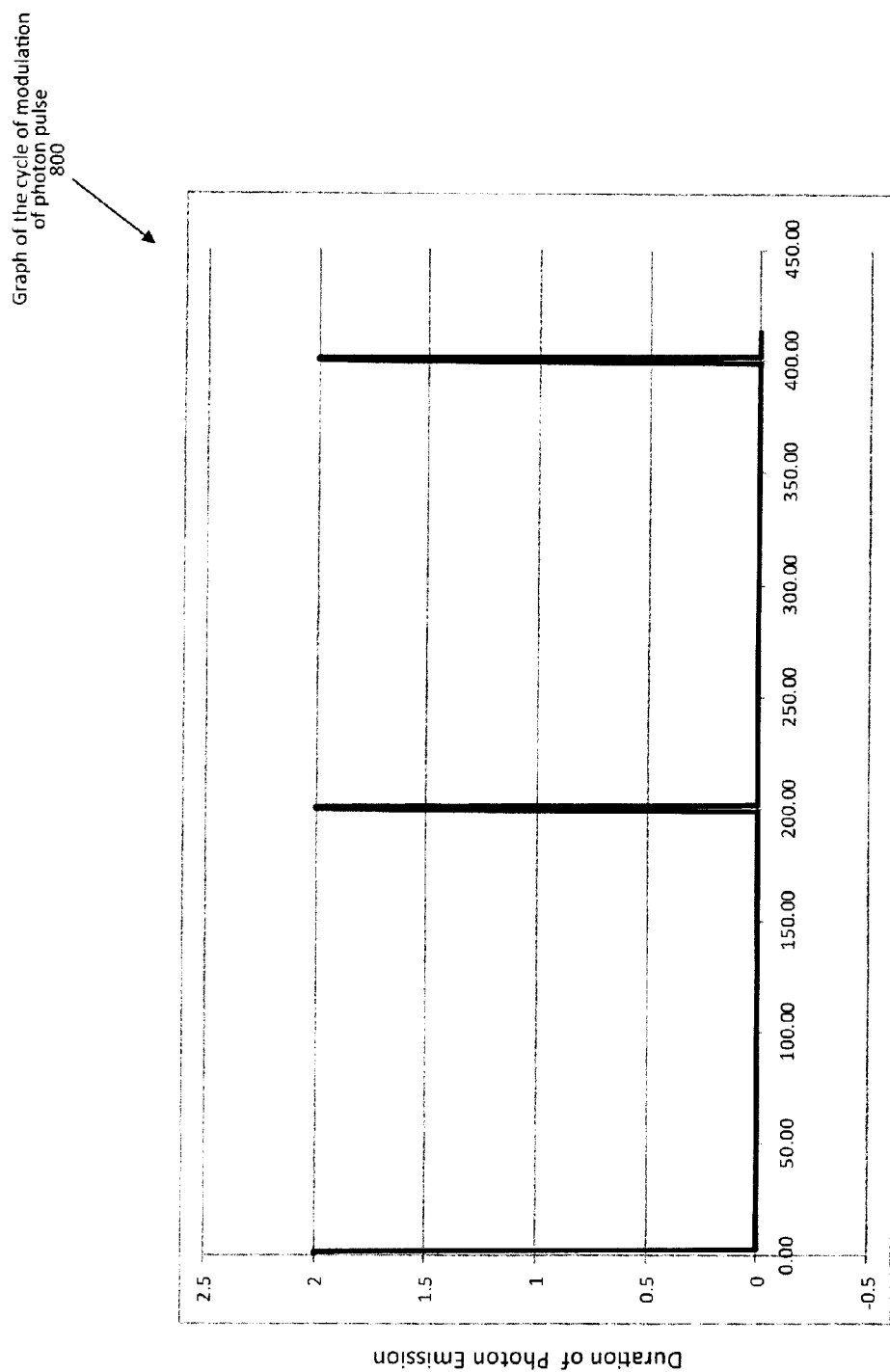
FIG. 8 is a graph of the cycle of modulation of a photon pulse.

FIG. 8 also shows the blue solid-state relay 706 sending a photon emission signal 136 to initiate a photon pulse of blue LEDs comprising a blue voltage 712 to an array of blue LEDs 716. The blue voltage 712 is then transmitted from the array of blue LEDs 716 and transmitted to a series of resistors 722, 726, 730, 736 and 740, such as a 150 ohm resistor, with each resistor 722, 726, 730, 736 and 740 connected to a ground 744.

The system of the present disclosure may be successfully employed with a wide variety of organisms, including but not limited to wide variety of algae, bacteria, fungi, gymnosperms, angiosperms and pteridophytes, cyanobacteria or eukaryotic green algae. This list of organisms may further include but is not limited to *Arthrospira* spp., *Spirulina* spp., *Calothrix* spp., *Anabaena flos-aquae*, *Aphanizomenon* spp., *Anadaena* spp., *Gleotrichia* spp., *Oscillatoria* spp., *Nostoc* spp., *Synechococcus elongatus*, *Synechococcus* spp., *Synechosystis* spp. PCC 6803, *Synechosystis* spp., *Spirulina plantensis*, *Chaetoceros* spp., *Chlamydomonas reinhardii*, *Chlamydomonas* spp., *Chlorella vulgaris*, *Chlorella* spp., *Cyclotella* spp., *Didymosphenia* spp., *Dunaliella tertiolecta*, *Dunaliella* spp., *Botryococcus braunii*, *Botryococcus* spp., *Gelidium* spp., *Gracilaria* spp., *Hantscia* spp., *Hematococcus* spp., *Isochrysis* spp., *Laminaria* spp., *Navicula* spp., *Pleurochrysis* spp. and *Sargassum* spp; citrus, table grapes, wine grapes, bananas, *papaya, Cannabis* sp., coffee, goji berries, figs, avocados, guava, pineapple, raspberries, blueberries, olives, pistachios, pomegranate, artichokes and almonds; vegetables such as artichokes, asparagus, bean, beets, broccoli, brussel sprouts, chinese cabbage, head cabbage, mustard cabbage, cantaloupe, carrots, cauliflower, celery, chicory, collard greens, cucumbers, daikon, eggplant, endive, garlic, herbs, honey dew melons, kale, lettuce (head, leaf, romaine), mustard greens, okra, onions (dry & green), parsley, peas (sugar, snow, green, black-eyed, crowder, etc.), peppers (bell, chile), pimento, pumpkin, radish, rhubarb, spinach, squash, sweet corn, tomatoes, turnips, turnip greens, watercress, and watermelons; flowering type bedding plants, including, but not limited to, *Ageratum, Alyssum, Begonia, Celosia, Coleus*, dusty miller, Fuchsia, Gazania, Geraniums, *gerbera* daisy, *Impatiens*, Marigold, *Nicotiana*, pansy/Viola, *Petunia, Portulaca, Salvia*, Snapdragon, *Verbena, Vinca*, and *Zinnia*; potted flowering plants including, but not limited to, African violet, Alstroemeria, Anthurium, Azalea, *Begonia*, Bromeliad, *Chrysanthemum, Cineraria*, Cyclamen, Daffodil/*Narcissus, Exacum, Gardenia, Gloxinia*, Hibiscus, Hyacinth, *Hydrangea*, Kalanchoe, Lily, Orchid, Poinsettia, *Primula*, regal *pelargonium*, rose, tulip, Zygocactus/Schlumbergera; foliage plants including, but not limited to, Aglaonema, Anthurium, Bromeliad, Opuntia, cacti and succulents, Croton, Dieffenbachia, Dracaena, Epipremnum, ferns, *ficus, Hedera* (Ivy), Maranta/Calathea, palms, Philodendron, *Schefflera*, Spathiphyllum, and *Syngonium*. cut flowers including, but not limited to, Alstroemeria, Anthurium, Aster, bird of paradise/*Strelitzia*, calla lily, carnation, *Chrysanthemum*, Daffodil/*Narcissus*, daisy, Delphinium, Freesia, *gerbera* daisy, ginger, *Gladiolus*, Godetia, *Gypsophila*, heather, iris, *Leptospermum*, Liatris, lily, *Limonium*, Lisianthus, Orchid, Protea, Rose, Statice, Stephanotis, Stock, Sunflower, Tulip; cut cultivated greens including, but not limited to, plumosus, tree fern, boxwood, soniferous greens, *Cordyline, Eucalyptus, hedera*/Ivy, holly, leatherleaf ferns, Liriope/Lilyturf, Myrtle, *Pittosporum*, Podocarpus; deciduous shade trees including, but not limited to, ash, birch, honey locust, linden, maple, oak, poplar, sweet gum, and willow; deciduous flowering trees including, but not limited to, *Amelanchier*, callery pea, crabapple, crapemyrtle, dogwood, flowering cherry, flowering plum, golden rain, hawthorn, *Magnolia*, and redbud; broadleaf evergreens including, but not limited to, Azalea, cotoneaster, *Euonymus*, holly, *Magnolia, Pieris*, Privet, *Rhododendron*, and *Viburnum*; coniferous evergreens including, but not limited to, Arborvitae, cedar, cypress, fir, hemlock, juniper, pine, spruce, yew; deciduous shrubs and other ornamentals including, but not limited to, buddleia, hibiscus, lilac, Spirea, *Viburnum*, Weigela, ground cover, *bougainvillea, clematis* and other climbing vines, and landscape palms; fruit and nut plants including, but not limited to, citrus and subtropical fruit trees, deciduous fruit and nut trees, grapevines, strawberry plants, other small fruit plants, other fruit and nut trees; cut fresh, strawberries, wildflowers, transplants for commercial production, and aquatic plants; pteridophyte plants including, but not limited to ferns and fungi including but not limited to basidiomycetes, ascomycetes, and sacchromycetes. The system of the present disclosure provides a photon pulse for both C3 and C4 photosystems as well as "CAM" plants (Crassulacean acid metabolism).

FIG. 8 is a graph showing an example the duration of a photon pulse versus the duration of the delay between photon pulses 800. As shown in FIG. 8 and previously described in FIGS. 1-7, an example of a photon pulse of the present disclosure is provided where a photon pulse is emitted from a photon emitter for two (2) milliseconds with a duration of delay of two hundred (200) milliseconds before a second photon pulse is emitted for two milliseconds. After the second of the two millisecond photon pulses, as shown in FIG. 8, there is again a duration of two hundred (200) milliseconds before a third photon pulse is emitted. This cycle of a two (2)-millisecond photon pulse with a two hundred millisecond delay between photon pulses may be repeated indefinitely or until the organism growing under and receiving the photon pulses has reached its desired size or maturity or is destroy or repaired. While in this descriptive example of a photon pulse of two milliseconds and a duration between photon pulses of 200 milliseconds, it should be understood that this description is applicable to any such system with other emissions of photon pulses over a period of time, excluding the standard analog frequency lighting emission standards of the United States of 60 Hz and Europe of 50 Hz. Examples of the photon pulse duration may include but is not limited to, 0.01 microseconds to 5000 milliseconds and all integers in between. The system of the present disclosure also allows for other durations between photon pulses including but not limited one microsecond to 24 hours (mimicking natural dark cycles), and all integers in between. The system of the present disclosure may be programmed to allow for variations of photon emission as well as variations of photon emission delay to allow for events such as extended dark cycles.

Figure 9:
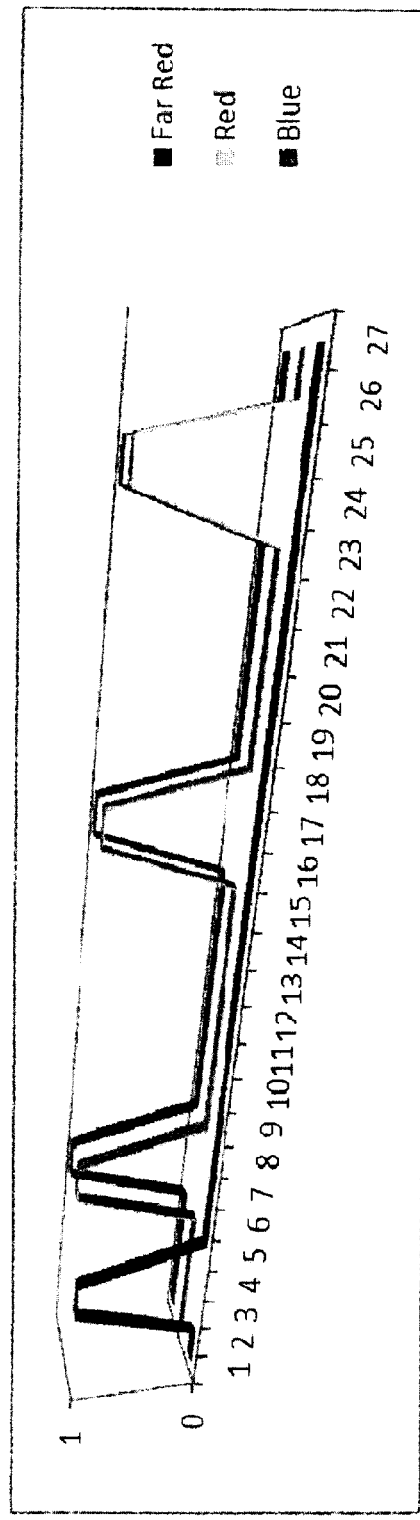
FIG. 9 is an example graph of the cycling of three individual photon pulses, with each pulse comprising a different wavelength band at different timing.

FIG. 9 is a graph showing an example of the duration of a photon pulse versus the duration of the delay between photon pulses of three color spectrums 900. The time scale on this chart is not to scale but serves as an example embodiment exhibiting the variation of color spectrum, frequency and duty cycle that may be utilized for growth or destruction of an organism as shown in as Options 10 and 11 in Examples 1-7. As shown in FIG. 9 and previously described in FIGS. 1-7, another example of the cycling of photon pulses of various color spectrum of the present disclosure is provided where photon pulses of three color spectrums are emitted from a photon emitter. As shown in the graph a far-red spectrum is pulsed first followed by a delay and then a dual pulse of a near red spectrum and a blue spectrum together is then dosed followed by a delay creating a first set of photon pulses. Next, a second set of dual pulses comprising of near red spectrum and blue spectrum are pulsed together again followed by a delay. After the delay, a near red spectrum and blue spectrum are pulsed together once again followed by an additional longer delay. This cycle may be repeated indefinitely or until the organism growing under and receiving the photon pulses has reached its desired size or maturity or is destroy or repaired or a change is desired for a new phase of growth or destruction. As discussed above, this example may also be used to increase seed germination rates in various types of plants. While in this descriptive example of a photon pulse set comprising offset pulsing of one color spectrum and two color spectrums, it should be understood that this description is applicable to any such system with other emissions of photon pulses over a period of time, as various combinations of pulses of color spectrums including but not limited to near red, far-red, infra-red, blue, yellow, orange and ultraviolet excluding the standard analog frequency lighting emission standards of the United States of 60 Hz and Europe of 50 Hz. Examples of the photon pulse duration between pulses of each individual color spectrum or color spectrum combinations may include but is not limited to, 0.01 microseconds to 5000 milliseconds and all integers in between. The system of the present disclosure also allows for other durations between pulses of each individual color spectrum or color spectrum combinations including but not limited to 0.1 microsecond to 24 hours, and all integers in between. The system of the present disclosure may be programmed to allow for variations of photon emission as well as variations of photon emission delay to allow for events such as extended dark cycles.

Figure 10:
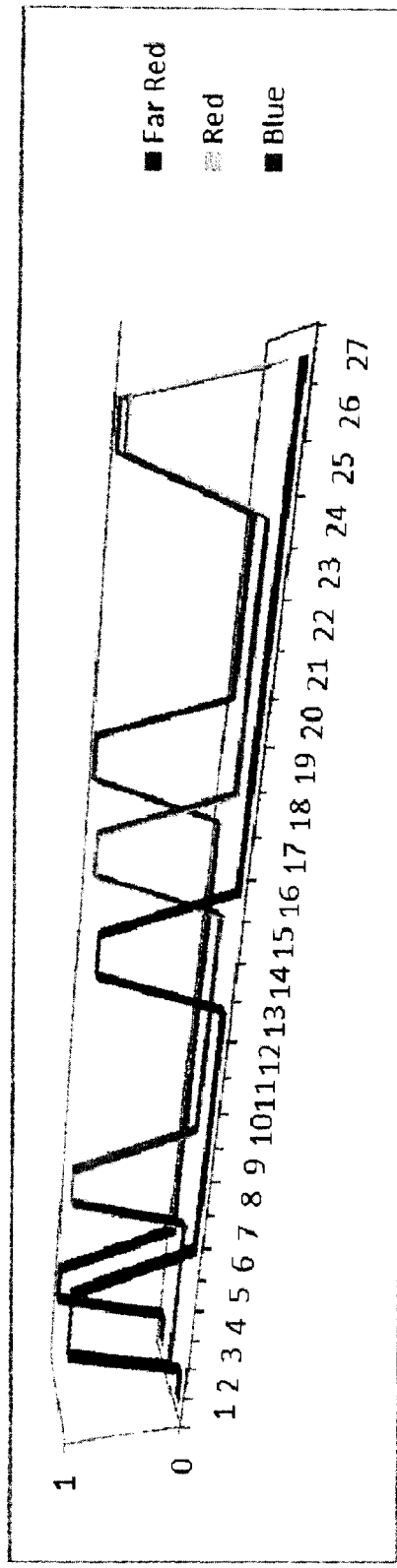
FIG. 10 is an example graph of the cycling of three individual photon pulses, with each pulse comprising a different wavelength band at different timing.

FIG. 10 is a graph showing an example of the duration of a photon pulse versus the duration of the delay between photon pulses of three color spectrums 1000. The time scale on this chart is not to scale but serves as an example embodiment exhibiting the variation of color spectrum, frequency and duty cycle that may be utilized for growth or destruction of an organism. As shown in FIG. 10 and previously described in FIGS. 1-7, another example of the cycling of photon pulses of various color spectrum of the present disclosure is provided where photon pulses of three color spectrums are emitted from a photon emitter. As shown in the graph a far red spectrum is pulsed simultaneously with a blue spectrum pulse. The far red spectrum is pulsed for twice the time as the blue spectrum. They are followed by a small delay and then a pulse of a near red spectrum is then dosed followed by a delay creating a first set of photon pulses. Next, a second set of pulses comprising first of far red spectrum then a near red spectrum followed by a blue spectrum are pulsed in rapid succession again followed by a delay. After the delay, a near red spectrum and blue spectrum are pulsed together once again followed by an additional longer delay. This cycle may be repeated indefinitely or until the organism growing under and receiving the photon pulses has reached its desired size or maturity or is destroy or repaired or a change is desired for a new phase of growth or destruction. As discussed above, this example may also be used to increase seed germination rates in various types of plants. While in this descriptive example of a photon pulse set comprising off set pulsing of one color spectrum and two color spectrums, it should be understood that this description is applicable to any such system with other emissions of photon pulses over a period of time, as various combinations of pulses of color spectrums including but not limited to near red, far red, infra-red, blue, yellow, orange and ultraviolet excluding the standard analog frequency lighting emission standards of the United States of 60 Hz and Europe of 50 Hz. Examples of the photon pulse duration between pulses of each individual color spectrum or color spectrum combinations may include but is not limited to, 0.01 microseconds to 5000 milliseconds and all integers in between. The system of the present disclosure also allows for other durations between pulses of each individual color spectrum or color spectrum combinations including but not limited 0.1 microsecond to 24 hours, and all integers in between. The system of the present disclosure may be programmed to allow for variations of photon emission as well as variations of photon emission delay to allow for events such as extends dark cycles.

Figure 11:
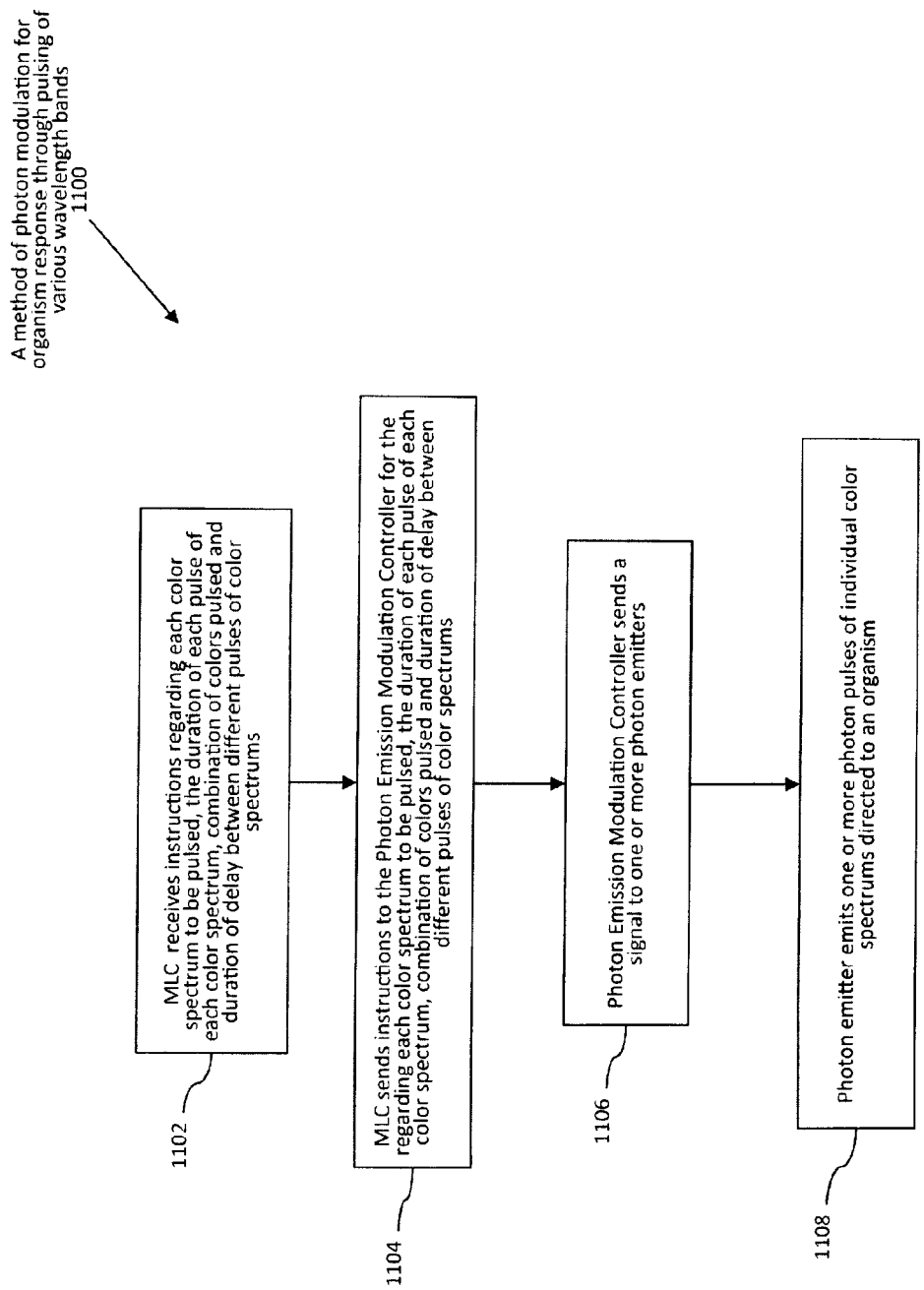
FIG. 11 is a flow diagram showing a method of photon modulation for organism growth through pulsing of various wavelength bands.

FIG. 11 is a flow diagram showing the method of modulation of individual color spectrums pulsed for organism growth 1100. As shown in FIG. 11, in step 1102, the master logic controller receives instructions regarding each individual color spectrum to be pulsed, the duration of each pulse of each color spectrum, the combination of colors to be pulsed and duration of delay between each color spectrum pulse. Instructions and information sent to the master logic controller may relate to the photon pulse duration of each color to be pulsed, photon pulse delay, intensity, frequency, duty cycle, organism type, state of maturity of the organism and the type of growth, destruction or repair that is desired to be induced, such as bud and flower formation, seed formation, sporting, fungal fruiting bodies, and hyphae formation. In step 1104, the master logic controller sends instructions to the photon emission modulation controller the regarding each color spectrum to be pulsed, the duration of each pulse of each color spectrum, combination of colors pulse and duration of delay between different color spectrums. In step 1106, the photon emission modulation controller sends at least one signal to one or more photon emitters capable of emitting pulses of one or more individual color spectrums toward an organism, such as near red LEDs, far-red LEDs, blue LEDs and yellow LEDs. In step 1108, one or more photon emitters emit one or more photon pulses of individual color spectrums directed to an organism.

Figure 12:
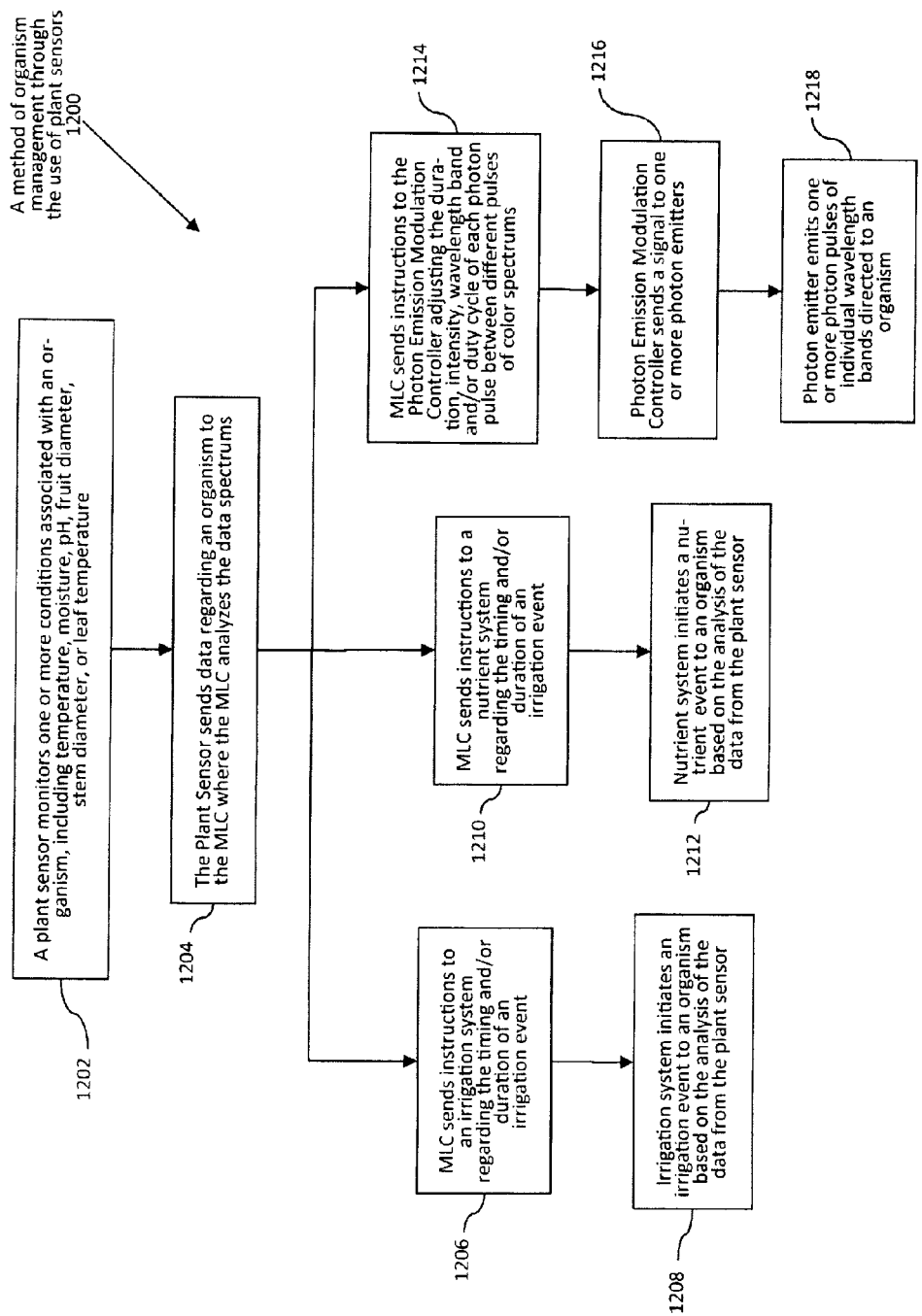
FIG. 12 is a flow diagram showing a method of organism growth, repair or destruction through the use of plant sensors.

FIG. 12 provides an additional embodiment of the present disclosure, showing a flowing diagram of the growth, repair or destruction of an organism based on information from plant sensors 1200. As shown in step 1202, a plant sensor monitors one or more conditions associated with growing environment of an organism. The conditions to be monitored by include but is not limited to the air or soil temperature associated with the plant or organism, soil moisture, humidity levels, soil pH, fruit diameter, stem diameter, leaf size, leaf shape, or leaf temperature. In step 1204, the plant sensor sends data regarding the growing conditions associated with the an organism to the MLC. The MLC then analyzes the data sent from the plant sensor or the analysis may be done by a third party software program that is remote to the system. In step 1206, based on the information from the plant sensor, the MLC sends instructions to an irrigation system, such as a drip or fog system, regarding the timing and/or duration of an irrigation event. In step 1208, irrigation system initiates an irrigation event to one or more organisms based on the analysis of the data from the plant sensor. As will be understood by one skilled in the art, the adjustment of the irrigation event can be on a micro level, such as an adjustment to the irrigation to one specific organism or the adjustment can be on a macro level such as an entire growth chamber or operation. In step 1210, based on the information from the plant sensor the MLC sends instructions to a nutrient system or nutrient source, such as a drip, nutrient film or nutrient injection system, regarding the timing and/or concentration of the nutrient to be distributed to an organism during a nutrient event. In step 1212, nutrient system initiates a nutrient event where nutrients are directed to an organism based on the analysis of the data from the plant sensor. As will be understood by one skilled in the art, the adjustment of the nutrient event can be on a micro level, such as an adjustment to the nutrients to one specific organism or the adjustment can be on a macro level such as an entire growth chamber or operation. In step 1214, based on the analysis of the data from the plant sensor, the MLC sends instructions to the photon emission modulation controller adjusting the duration, intensity, color spectrum and/or duty cycle of each photon pulse between different pulses of color spectrums to a specific organism or to a group of organisms. In step 1216, the photon emission modulation controller sends a signal to one or more photon emitters adjusting the duration, intensity, color spectrum and/or duty cycle of each photon pulse between different pulses of color spectrums to a specific organism or to a group of organisms. In step 1218, based on the signal received from the photon emission modulation controller, one or more photon emitters emit one or more photon pulses of individual color spectrums directed to an organism or a group of organisms.

EXAMPLES

The following examples are provided to illustrate further the various applications and are not intended to limit the invention beyond the limitations set forth in the appended claims.

Example 1

Table 1 shows the growth rate of two sets of plants over time (beans, *Phaseolus vulgaris* var. *nanus*). One set of plants was grown under the growth system of the present invention and one set of plants grown under a conventional plant grow light system (a 60 watt incandescent growing light). Plant growth was measured by measuring the height of each plant in millimeters. The plants were grown under an automated system where the plants grown under the photon modulation system of the present invention was established at a two-millisecond photon pulse of near-red, blue, and yellow with a duration of the delay between pulses of 200 milliseconds. This was then repeated with a two-millisecond photon pulse of far-red offset by 100 milliseconds with a duration of the delay between pulses of 200 milliseconds. This cycle was then repeated indefinitely for 24 hrs/day This rate of photon pulse and photon pulse delay is estimated to have an energy usage of less than 1% of the energy used the by conventional grow light. The plants grown under the conventional growing light were exposed to the light of the conventional growing light for a period of 12 hours per day. Plants were grown in nine (9) oz. plastic cups with small holes located at the base of the cup for drainage. Seed were planted in a soil mixture (MiracleGro Moisture control potting mix).

A manual watering system provided an adequate amount of moisture for the plants. The plant containers were placed in a black container or box with a lid that did not allow light to enter unless the lid was removed. A photon emitter comprising an array of LEDs or the 60 watt grow lights were affixed to the top of the respective black containers. The LEDs comprised an array of red LEDs (640 nm and 700 nm), an array of yellow round LEDs (590 nm) and an array of blue round LEDs (450 nm). The photon emitter was wired to a solid-state relay, comprising a Magnacraft 70S2 3V solid-state relay, to allow for communication between the photon emitter and the solid-state relay. The solid-state relay was in communication with a central processing unit to provide input and output instructions to the solid-state relay. The central processing unit was programmed to instruct the solid-state relay to modulate the signals to the photon emitter in order to produce a two millisecond pulse of photons every 200 milliseconds.

As shown in Table 1, column one provides the type of growing system used. Column two provides the type of plant and the individual plant number for each plant. Columns 3 to 8 provide the day of measurement of the plant from the original planting of the seeds. As shown in Table 1, using the photon modulation growing system, within day eight from planting Bean1, Bean2 and Bean3 had grown to a height between 77 mm and 136 mm. By day fourteen Bean1, Bean2 and Bean3 grown under the photon modulation growth system to a height between 200 mm and 220 mm. In comparison, under the conventional 60 watt growing lights by day eight Bean1 and Bean2 had grown between 155 mm and 185 mm and by day fourteen Bean1, Bean2 and Bean3 had grown between 160 mm and 220 mm. This data shows that the photon modulation growing system, using less than 1% of the energy of the conventional growing system, is able to grow bean plants equally as well or better when compared to a conventional growing system.

TABLE 1

Plant height measured in millimeters when grown under photon modulation at a rate of a two millisecond photon pulse every two hundred milliseconds when compared to a conventional growth light

|  |  | Day 6 | Day 7 | Day 8 | Day 12 | Day 13 | Day 14 |
|---|---|---|---|---|---|---|---|
| Photon Modulation System | Bean1 | No data | 31 | 136 | 205 | 210 | 220 |
|  | Bean2 | No data | 77 | 133 | 190 | 195 | 200 |
|  | Bean3 | No data | No data | 77 | 195 | 210 | 210 |
| 60 W incandescent grow light | Bean1 | 120 | 153 | 185 | 220 | 220 | 220 |
|  | Bean2 | 87 | 135 | 155 | 180 | 160 | 160 |
|  | Bean3 | No data | No data | No data | 150 | 160 | 160 |

Example 2

Table 2 shows the leaf size of two sets of plants over time (beans, *Phaseolus vulgaris* var. *nanus*) with one set of plants grown under the photon modulation growth system of the present invention and one set of plants grown under a conventional growing light (a 60 watt incandescent growing light) by measuring the leaf size of each plant in millimeters. Example 1 is repeated and as shown in Table 2, a measurement of leaf size in millimeters is provided with column one providing the type of growing system used. Column 2 provides the type of plant and the individual plant number. Columns 3 to 8 provides the day of leaf measurement from the date of the original planting of the seeds. As shown in Table 2, using the photon modulation growing system, within day eight from planting Bean1, Bean2 and Bean3 had a leaf size between 50 mm×47 mm and 59 mm×55 mm and by day fourteen Bean1, Bean2 and Bean3 had a leaf size between 55×52 mm and 64 mm×58 mm. In comparison, under the conventional 60 watt growing lights by day eight Bean1 and Bean3 had a leaf size between 26 mm×22 mm and 57 mm×50 mm and by day fourteen Bean1 and Bean3 had a leaf size between 33 mm×30 mm and 62 mm×55 mm. This data shows that bean leaf size grown under the photon modulation growing system, using less than 1% of the energy of the conventional growing system, is able to grow beans equally as well or better when compared to a conventional growing system.

TABLE 2

Plant leaf size measured in millimeters when grown under photon modulation at a rate of a two millisecond photon pulse every two hundred milliseconds when compared to conventional growth lights

|  |  | Day 6 | Day 7 | Day 8 | Day 12 | Day 13 | Day 14 |
|---|---|---|---|---|---|---|---|
| Photon Modulation System | Bean1 | No data | No data | 50 × 47 | 51 × 48 | 55 × 50 | 55 × 52 |
|  | Bean2 | No data | 30 × 25 | 59 × 55 | 59 × 55 | 61 × 55 | 64 × 58 |
|  | Bean3 | No data | No data | 52 × 50 | 54 × 51 | 56 × 52 | 56 × 55 |
| 60 W incandescent grow light | Bean1 | 32 × 25 | 38 × 31 | 57 × 50 | 59 × 53 | 62 × 55 | 62 × 55 |
|  | Bean2 | 31 × 23 | 34 × 30 | 50 × 43 | 53 × 45 | 55 × 45 | 57 × 45 |
|  | Bean3 | No data | No data | 26 × 22 | 28 × 23 | 30 × 27 | 33 × 30 |

Example 3

Figure 13:
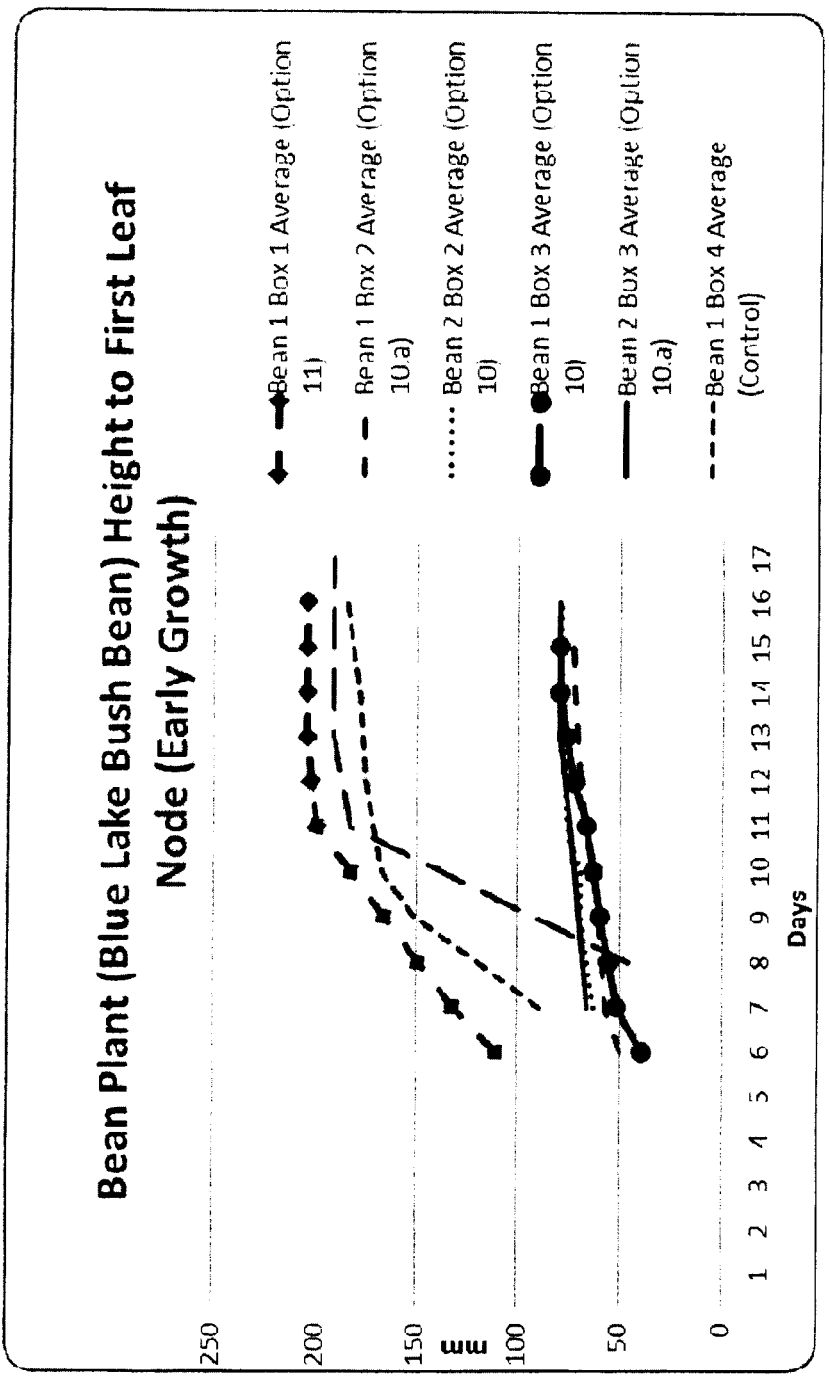
FIG. 13 is a graph showing the height of beans, (*Phaseolus vulgaris* var. *nanus*) in millimeters to the first leaf node.

FIG. 13, shows the height of beans, (*Phaseolus vulgaris* var. *nanus*) in millimeters to the first leaf node. As shown in FIG. 13, Box 1 shows beans grown under the color spectrum photon emissions of Option 11, where Option 11 is based on the example photon emission shown in FIG. 9, however the duration of the pulse of near red is extend and the frequency of the all three pulses (far red, near red and blue) are not drawn to scale. Box 2 and Box 3 show beans grown under color spectrum emissions of Options 10, where Option 10 is based on the example photon emission shown in FIG. 9, however the duration of the pulse of far red is extend and the duty cycle of Option 10 of the all three pulses (far red, near red and blue) are not drawn to scale, and Options 10a. Box 4 shows beans grown under color spectrum emissions of a control comprising plants grown under a conventional growing light (a 60 watt incandescent growing light) with no modulation of pulses of individual color spectrums.

As shown in FIG. 13, data related to measurement to the first leaf node began six days after planting of the seeds. Both plants grown under the control and Option 11 had consistent growth of the plant over 16 days, with a maximum height of 200 mm. However, plants grown under Option 10 and Option 10a consistently had a shorter height to the first leaf node over the entire period of measurement with an initial height less than 50 mm and a maximum height less than 100 mm.

The data of FIG. 13 shows the ability of the system of the present disclosure to control plant growth through the modulation of pulses of individual color spectrums to a plant.

Example 4

Figure 14:
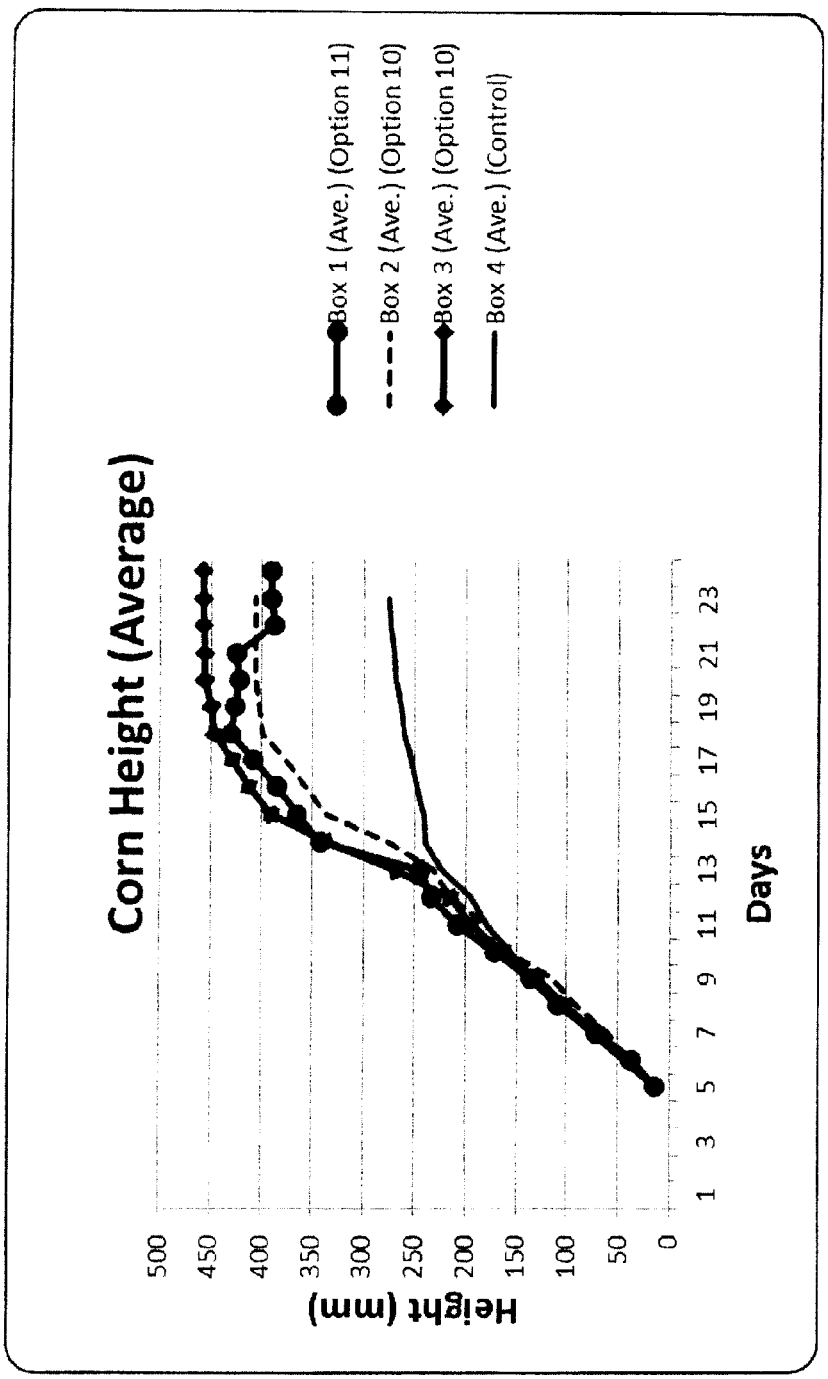
FIG. 14 is a graph showing average corn (*Zea mays*) height in millimeters for plants grown under the color spectrum photon emissions of Option 11, Option 10 and a control).

FIG. 14 shows average corn (*Zea mays*) height in millimeters for plants grown under the color spectrum photon emissions of Option 11, Option 10 and a control. As previously discussed, Option 10 and Option 11 are both based on the example photon emission shown in FIG. 9. Box 2 and Box 3 show beans grown under color spectrum emissions of Options 10 Plants grown in Box 1 were grown in the color spectrum photon emissions of Option 11. Plants grown in Box 2 and Box 3 show beans grown under color spectrum emission of Option 10. Plants grown in Box 4 were grown under color spectrum emissions of a control comprising plants grown under a conventional growing light (a 60 watt incandescent growing light) with no modulation of pulses of individual color spectrums.

As shown in FIG. 14, plants grown in all four boxes showed measureable growth five days after planting. Plants grown under Option 10 and Option 11 showed consistent growth, with a measurable increase in growth after 13 days over plants grown under the control. Plants grown under Option 10 and Option 11 had a maximum height over 450 mm with a lower maximum height of just under 400 mm. Conversely, plants grown under the control had a maximum height under 300 mm.

The data of FIG. 14 shows the ability of the system of the present disclosure to increase and improve plant growth through the modulation of pulse of individual color spectrums to a plant.

Example 5

Figure 15:
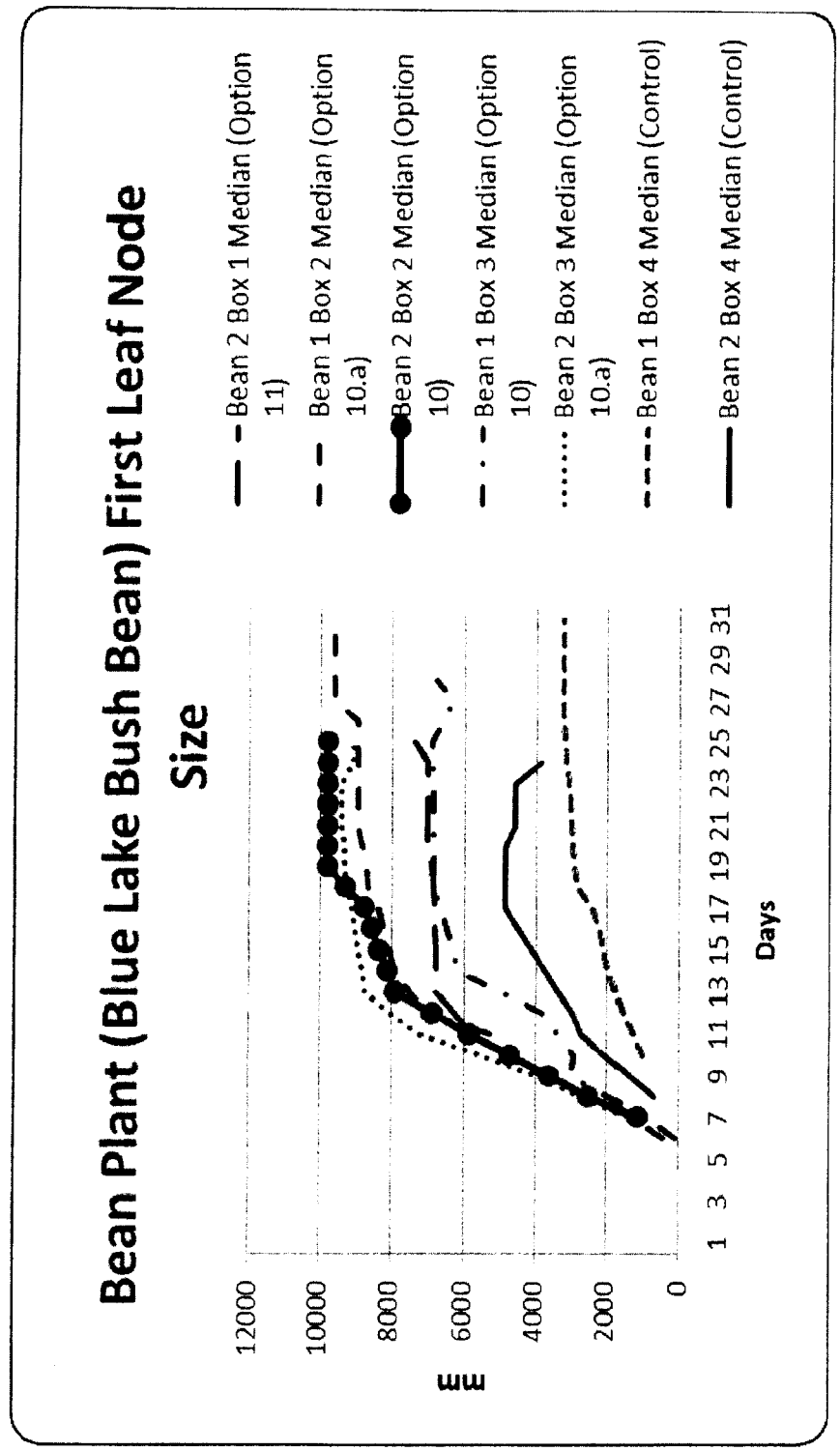
FIG. 15 is a graph showing the size of the first node of beans, (*Phaseolus vulgaris* var. *nanus*) in millimeters.

FIG. 15 shows the size of the first node of beans, (*Phaseolus vulgaris* var. *nanus*) in millimeters. As shown in FIG. 15, Box 1 shows beans grown under the color spectrum photon emissions of Option 11. As previously discussed, Option 10 and Option 11 are both based on the example photon emission shown in FIG. 9. Box 2 and Box 3 show beans grown under color spectrum emissions of Options 10 and Options 10a. Box 4 shows beans grown under color spectrum emissions of a control comprising plants grown under a conventional growing light (a 60 watt incandescent growing light) with no modulation of pulses of individual color spectrums.

As shown in FIG. 15, data related to measurement to the size of the first leaf node began approximately six days after planting of the seeds. Both plants grown under the Option 10, Option 10a and Option 11 had consistent growth and first node size over 16 days, with a maximum first node size of 10000 mm. However, plants grown under the control had significantly smaller first node sizes with a first node size of 4000 mm or less.

The data of FIG. 15 shows the ability of the system of the present disclosure to improve the quality plant growth through the modulation of pulses of individual color spectrums to a plant.

Example 6

Figure 16:
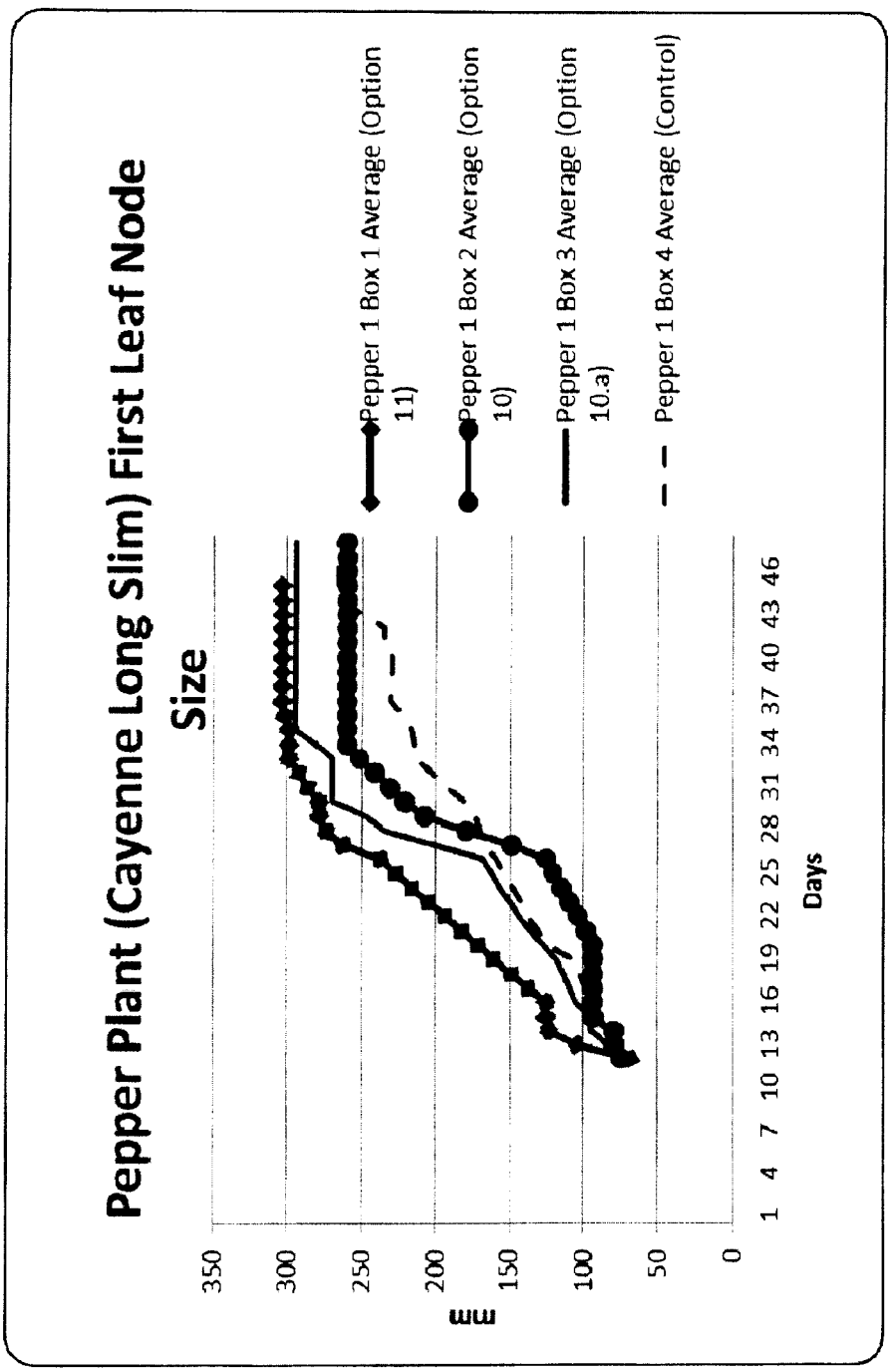
FIG. 16 is a graph showing the size of the first leaf node of peppers, (Cayenne) in millimeters.

FIG. 16 shows the size of the first leaf node of peppers, (Cayenne) in millimeters. As shown in FIG. 16, Box 1 shows peppers grown under the color spectrum photon emissions of Option 11. As previously discussed, Option 10 and Option 11 are both based on the example photon emission shown in FIG. 9. Box 2 and Box 3 show peppers grown under color spectrum emissions of Options 10 and Options 10a. Box 4 shows peppers grown under color spectrum emissions of a control comprising plants grown under a conventional growing light (a 60 watt incandescent growing light) with no modulation of pulses of individual color spectrums.

As shown in FIG. 16, data related to measurement to the size of the first leaf node began approximately ten days after planting of the seeds. Both plants grown under the Option 10, Option 10a and Option 11 had consistent growth and first node size over 16 days, with a maximum first leaf node size of 300 mm. However, plants grown under the control had significantly smaller first node sizes with a first node size of 4000 mm or less.

The data of FIG. 16 shows the ability of the system of the present disclosure to improve the quality plant growth through the modulation of pulses of individual color spectrums to a plant.

Example 7

Figure 17:
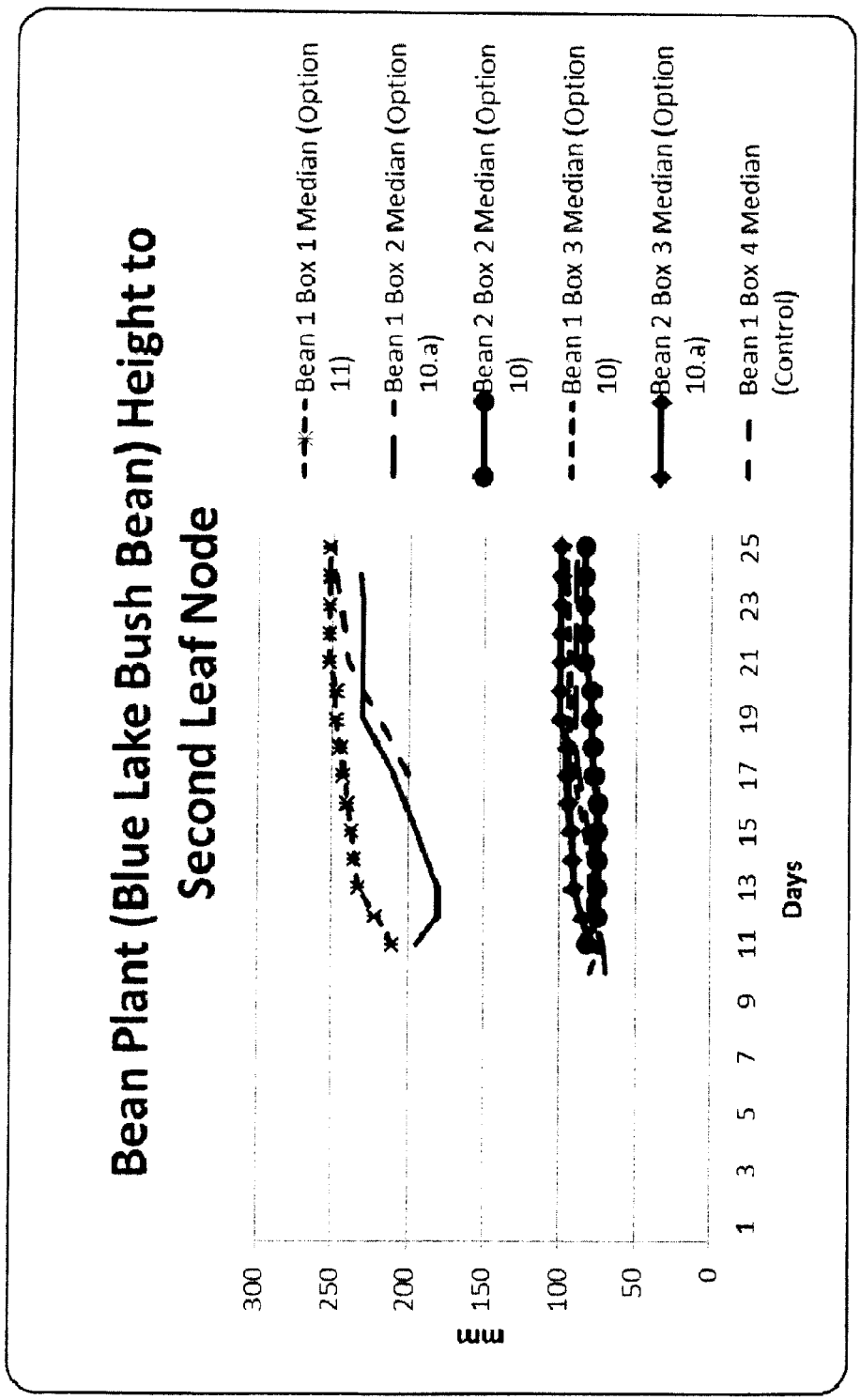
FIG. 17 is a graph showing the height in millimeters to the second leaf node of beans, (*Phaseolus vulgaris* var. *nanus*).

FIG. 17 shows the height in millimeters to the second leaf node of beans, (*Phaseolus vulgaris* var. *nanus*). As shown in FIG. 17, Box 1 shows beans grown under the color spectrum photon emissions of Option 11. As previously discussed, Option 10 and Option 11 are both based on the example photon emission shown in FIG. 9. Box 2 and Box 3 show beans grown under color spectrum emissions of Options 10 and Options 10a. Box 4 shows beans grown under color spectrum emissions of a control comprising plants grown under a conventional growing light (a 60 watt incandescent growing light) with no modulation of pulses of individual color spectrums.

As shown in FIG. 17, data related to measurement to the second leaf node began approximately ten days after planting of the seeds. Both plants grown under the control and Option 11 had consistent growth of the plant over 25 days, with a maximum height of 250 mm. However, plants grown under Option 10 and Option 10a consistently had a shorter height to the second leaf node over the entire period of measurement with an average height between 50 mm and 100 mm.

The data of FIG. 17 shows the ability of the system of the present disclosure to control plant growth through the modulation of pulses of individual color spectrums to a plant.

The foregoing description of the invention has been presented for purposes of illustration and description. It is not intended to be exhaustive or to limit the invention to the precise form disclosed, and other modifications and variations may be possible in light of the above teachings. The embodiment was chosen and described in order to best explain the principles of the invention and its practical application to thereby enable others skilled in the art to best utilize the invention in various embodiments and various modifications as are suited to the particular use contemplated. It is intended that the appended claims be construed to include other alternative embodiments of the invention except insofar as limited by the prior art.

What is claimed is:

1. A method for inducing a desired response in an organism wherein said method comprises:

providing at least two photon emitters;

providing at least one photon emission modulation controller in communication with said at least two photon emitters;

communicating a command from said at least one photon emission modulation controller to said at least two photon emitters;

providing a photon signal to said organism, wherein said photon signal comprises two or more independent components, wherein said two or more independent components comprise:

a first independent component of a repetitive first modulated photon pulse group, wherein said first modulated photon pulse group has one or more first photon pulse ON durations with one or more first intensities, has one or more first photon pulse OFF durations, and a first wavelength color;

wherein said one or more durations of said first photon pulse ON is between 0.01 microseconds and 5000 milliseconds and wherein the one or more durations of the first photon OFF is between is between 0.1 microseconds and 24 hours;

and a second independent component of a repetitive second modulated photon pulse group, wherein said second modulated photon pulse group has one or more second photon pulse ON durations with one or more second intensities, has one or more second photon pulse OFF durations, and a second wavelength color;

wherein said one or more durations of said second photon pulse ON is between 0.01 microseconds and 5000 milliseconds and wherein the one or more durations of the second photon OFF is between is between 0.1 microseconds and 24 hours;

wherein the first independent component and the second independent component are produced within said signal simultaneously;

wherein the second modulated photon pulse group is different from the first modulated photon pulse group; and emitting said signal toward said organism, wherein the combined effect of the first photon pulse group and the second photon pulse group of the signal produces a desired response from said organism.

2. The method of claim 1, further comprising:

a third or more independent component of a repetitive third or more modulated photon pulse group, wherein said third or more modulated photon pulse group has one or more third or more photon pulse ON durations with one or more third or more intensities, has one or more third or more photon pulse OFF durations, and a third or more wavelength color;

wherein the one or more third or more photon pulse ON durations are between 0.01 microseconds and 5000 milliseconds and wherein the one or more third or more photon pulse OFF durations are between 0.1 microseconds and 24 hours;

wherein the third or more independent components, the first independent component and the second independent component are produced within said signal simultaneously;

wherein the repetitive third or more modulated photon pulse group is different from the second modulated photon pulse group and the first modulated photon pulse group;

and emitting said signal toward said organism, wherein the combined effect of the repetitive third or more modulated photon pulse group, the first modulated photon pulse group and the second modulated photon pulse group of the signal produces a desired response from said organism.

3. The method of claim 2, wherein the duty cycle of said third or more modulated photon pulse group ranges between 0.1% to 93%.

4. The method of claim 2, each of the one or more additional photon pulse OFF durations of the third or more modulated photon pulse group is different.

5. The method of claim 2, each of the one or more additional photon pulse ON durations of the third or more modulated photon pulse group is different.

6. The method of claim 2, wherein said components of said third or more modulated photon pulse group is specifically tuned to a desired response from said organism.

7. The method of claim 2, wherein said each additional wavelength color of said third or more modulated photon pulse group is chosen from the group consisting of near red, far-red, blue, infra-red, yellow, orange, green and ultra-violet.

8. The method of claim 2, wherein said each additional wavelength color of said third or more modulated photon pulse group has a wavelength between 0.1 nm and 1 cm.

9. The method of claim 2, wherein said third or more modulated photon pulse group further comprises one or more additional intensities.

10. The method of claim 2, wherein the one or more durations of the third or more pulse ON are different from the one or more durations of the third or more photon pulse OFF.

11. The method of claim 1, further comprising:
providing a master logic controller in communication with said at least one photon emission modulation controller, wherein said master logic controller sends commands to said at least one photon emission modulation controller controlling the one or more first photon pulse ON duration, the one or more first photon pulse OFF duration, the first photon pulse intensity, and the first photon pulse wavelength color and said one or more second photon pulse ON duration, the one or more second photon pulse delay OFF duration, the second photon pulse intensity, and the second photon pulse wavelength color from said at least two photon emitters.

12. The method of claim 11, further comprising:
providing a master logic controller in communication with said at least one photon emission modulation controller, wherein said master logic controller sends commands to said at least one photon emission modulation controller controlling the components of said third or more modulated photon pulse group.

13. The method of claim 1, wherein said at least two photon emitters is selected from the group consisting of incandescent (Tungsten-halogen and Xenon), Fluorescent (CFL's), high intensity discharge (Metal Halide, High-Pressure Sodium, Low-Pressure Sodium, Mercury Vapor), sunlight, and light emitting diode.

14. The method claim 1, further comprising:
providing a power consumption sensor in communication with said master logic controller;
monitoring the power usage of said at least two photon emitters;
communicating said power consumption from said power consumption sensor to a host external to the master logic controller.

15. The method of claim 1, wherein said at least one photon emission modulation controller is selected from the group consisting of a solid-state relay, a metal-oxide-semiconductor field-effect transistor, a field-effect transistor, a zener diode, optical chopper and a device that induces modulation of said first modulated photon pulse group and said second modulated photon pulse group.

16. The method of claim 1, wherein said first wavelength color of said first modulated photon pulse group is chosen from the group consisting of near red, far-red, blue, infra-red, yellow, orange, green and ultra-violet.

17. The method of claim 1, wherein said second wavelength color of said second modulated photon pulse group is chosen from the group consisting of near red, far-red, blue, infra-red, yellow, orange, green and ultra-violet.

18. The method of claim 1, wherein said first wavelength color of said first modulated photon pulse group has a wavelength between 0.1 nm and 1 cm.

19. The method of claim 1, wherein said second wavelength color of said second modulated photon pulse group photon pulse has a wavelength between 0.1 nm and 1 cm.

20. The method of claim 1, wherein said first ON duration with one or more intensities, first duration OFF, and first wavelength color of said first modulated photon pulse group is the same as said second ON duration with one or more second intensities, second OFF duration, and second wavelength color of said second modulated photon pulse group.

21. The method of claim 1, further comprising
providing at least one sensor;
monitoring at least one condition associated with said organism, wherein said at least one condition associated with said organism is an environmental conditional associated with said organism or a physiological condition associated with said organism; and
communicating data regarding said condition from said at least one sensor to said master logic controller.

22. The method of claim 21, further comprising
adjusting said duration, intensity, wavelength band and duty cycle of said at least one first photon pulse and said duration, intensity, wavelength band and duty cycle from said at least one additional photon pulse from said at least one photon emitter based upon said data from said at least one sensor.

23. The method of claim 21, further comprising
providing an irrigation source in communication with said master logic controller, wherein said irrigation source provides irrigation events to said organism.

24. The method of claim 23, further comprising:
initiating an irrigation event from said irrigation source to said organism based on based upon said data from said at least one sensor.

25. The method of claim 24, wherein said master logic controller determines the timing of said irrigation event based upon said data from said at least one sensor.

26. The method of claim 24, wherein said master logic controller determines the duration of said irrigation event based upon said data from said at least one sensor.

27. The method of claim 21, further comprising
providing a nutrient source in communication with said master logic controller, wherein said nutrient source provides nutrient events to said organism.

28. The method of claim 27, further comprising:
initiating a nutrient event from said nutrient source to said organism based on based upon said data from said at least one sensor.

29. The method of claim 28, wherein said master logic controller determines the timing of said nutrient event based upon said data from said at least one sensor.

30. The method of claim 28, wherein said master logic controller determines the amount of nutrients directed toward said organism during said nutrient event based upon said data from said at least one sensor.

31. The method of claim 21, wherein said at least one sensor is selected from the group consisting of a stem diameter sensor, a fruit diameter sensor, a temperature sensor, a relative-rate sap sensor, an infrared sensor, a gas, a photorespiration sensor, a respiration sensor, a near-infrared sensor, camera, a pH sensor and combinations thereof.

32. The method of claim 1, wherein said organism is selected from the group comprising: bacteria, cyanobacteria, basidiomycetes, ascomycetes, sacchromycetes, angiosperms, pteridophytes, gymnosperms, cyanobacteria, diatoms, photosynthetic unicells, eukaryotic green algae, organisms within the kingdom Animalia, and tissue thereof.

33. The method of claim 1, wherein all additional or supplemental light is obstructed from said organism.

34. The method of claim 1, wherein said emission of said signal is a supplemental source of photons.

35. The method of claim 1, wherein said desired response from said organism is a photosynthetic response.

36. The method of claim 1, wherein said desired response from said organism is a phototrophic response.

37. The method of claim 1, wherein said desired response from said organism is a photoperiodic response.

38. The method of claim 1, wherein said first modulated photon pulse group has a change in light quantum of at least 5%.

39. The method of claim 1, wherein said second modulated photon pulse group photon pulse has a change in light quantum of at least 5%.

40. The method of claim 1, wherein the duty cycle of said first modulated photon pulse group and second modulated photon pulse group ranges between 0.1% to 93%.

41. The method of claim 1, wherein said response is response a non-naturally stimulated response selected from growth, repair and destruction.

42. The method of claim 1, wherein said first photon pulse ON duration with one or more first intensities, said first photon pulse OFF duration, and said first wavelength band of said first modulated photon pulse group is specifically tuned to a desired response from said organism.

43. The method of claim 1, wherein said second photon pulse ON duration with one or more second intensities, said second photon pulse OFF duration, said second wavelength band of said second modulated photon pulse group duty cycle is specifically tuned to a desired response from said organism.

44. The method of claim 1, wherein said method reduces the power used to induce a desired response in an organism by at least 50% when compared to conventional growing systems.

45. The method of claim 1, wherein each of the one or more first photon pulse OFF durations of the first modulated photon pulse group is a different duration.

46. The method of claim 1, wherein each of the one or more second photon pulse OFF durations of the second modulated photon pulse group is a different duration.

47. The method of claim 1, wherein each of the one or more first photon pulse ON durations of the first modulated photon pulse group is a different duration.

48. The method of claim 1, wherein each of the one or more second photon pulse ON durations of the second modulated photon pulse group is a different duration.

49. The method of claim 1, wherein the one or more durations of the first pulse ON are different from the one or more durations of the first photon pulse OFF.

50. The method of claim 1, wherein the one or more durations of the second pulse ON are different from the one or more durations of the second photon pulse OFF.

* * * * *

UNITED STATES PATENT AND TRADEMARK OFFICE
CERTIFICATE OF CORRECTION

PATENT NO. : 9,526,215 B2
APPLICATION NO. : 14/197949
DATED : December 27, 2016
INVENTOR(S) : Jon Daren Suntych It is certified that error appears in the above-identified patent and that said Letters Patent is hereby corrected as shown below:

In the Claims

The following claims should read:

4. The method of claim 2, wherein each of the one or more additional photon pulse OFF durations of the third or more modulated photon pulse group is different.

5. The method of claim 2, wherein each of the one or more additional photon pulse ON durations of the third or more modulated photon pulse group is different.

24. The method of claim 23, further comprising: initiating an irrigation event from said irrigation source to said organism based upon said data from said at least one sensor.

28. The method of claim 27, further comprising: initiating a nutrient event from said nutrient source to said organism based upon said data from said at least one sensor.

31. The method of claim 21, wherein said at least one sensor is selected from the group consisting of a stem diameter sensor, a fruit diameter sensor, a temperature sensor, a relative-rate sap sensor, an infrared sensor, a gas sensor, a photorespiration sensor, a respiration sensor, a near-infrared sensor, a camera, a pH sensor and combinations thereof.

41. The method of claim 1, wherein said response is a non-naturally stimulated response selected from growth, repair and destruction.

Signed and Sealed this
Twenty-ninth Day of August, 2017

Joseph Matal
*Performing the Functions and Duties of the*
*Under Secretary of Commerce for Intellectual Property and*
*Director of the United States Patent and Trademark Office*